US008211666B2

(12) United States Patent
Clapham et al.

(10) Patent No.: US 8,211,666 B2
(45) Date of Patent: Jul. 3, 2012

(54) SPERM-SPECIFIC CATION CHANNEL, CATSPER1, AND USES THEREFOR

(75) Inventors: David E. Clapham, Wellesley, MA (US); Dejian Ren, Wynnewood, PA (US)

(73) Assignee: Children's Medical Center Corporation, Boston, MA (US)

( * ) Notice: Subject to any disclaimer, the term of this patent is extended or adjusted under 35 U.S.C. 154(b) by 1173 days.

(21) Appl. No.: 10/697,863

(22) Filed: Oct. 30, 2003

(65) Prior Publication Data

US 2004/0157292 A1    Aug. 12, 2004

Related U.S. Application Data

(63) Continuation of application No. PCT/US02/13847, filed on May 3, 2002.

(60) Provisional application No. 60/327,167, filed on Oct. 4, 2001, provisional application No. 60/228,402, filed on May 3, 2001.

(51) Int. Cl.
*C12N 15/00* (2006.01)
*C12N 15/85* (2006.01)
*C12N 5/06* (2006.01)
*C12N 1/21* (2006.01)
*C12N 5/08* (2006.01)
*C12N 1/19* (2006.01)
*C07H 21/04* (2006.01)
*C07K 14/00* (2006.01)

(52) U.S. Cl. ............... 435/69.1; 435/320.1; 435/325; 435/252.1; 435/348; 435/366; 435/254.2; 536/23.1; 536/23.5; 530/350

(58) Field of Classification Search .............. None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 5,459,039 | A | 10/1995 | Modrich et al. |
| 5,498,531 | A | 3/1996 | Jarrell |
| 6,159,478 | A | 12/2000 | Haanes et al. |
| 6,787,309 | B2 | 9/2004 | Splawski et al. |
| 2001/0039335 | A1 | 11/2001 | Jacobs et al. |
| 2002/0082210 | A1 | 6/2002 | Curtis |

FOREIGN PATENT DOCUMENTS

| WO | WO 00/61624 | 10/2000 |
| WO | WO-00/66735 | 11/2000 |
| WO | WO 01/07611 A2 | 2/2001 |
| WO | WO 01/54477 A2 | 8/2001 |
| WO | WO 01/75067 A2 | 10/2001 |
| WO | WO-01/88090 | 11/2001 |
| WO | WO-01/90304 | 11/2001 |
| WO | WO 02/090567 A2 | 11/2002 |
| WO | WO 03/089583 A2 | 10/2003 |
| WO | WO 03/091434 A1 | 11/2003 |
| WO | WO 03/099865 A1 | 12/2003 |

OTHER PUBLICATIONS

N.A., Suppl 1, Trends Pharmacol. Sci., 1997, 18: 77-84.*
Lehmann-Horn et al., 1999, Physiol Rev 79(4): 1317-1372.*
Sanger Centre, 1998, Science, 282: 2012-2018.*
Hillier, et al, 1997, Accession No. AA416682.1.*
Nikpoor, et al, 2004, CatSper gene expression in postnatal development of mouse testis and in subfertile men with deficient sperm motility. Human Reprod. 19(1): 124-128.*
Hillier, et al (1997) Accession No. AA416577.1. Accessed Oct. 29, 2010 at http://www.ncbi.nlm.nih.gov/nucest/AA416577.1?report=gbwithparts&log$=seqview.*
Database EMBL, May 30, 2000, XP002306734, Database Accession No. AP000586.
Database EMBL, Mar. 3, 2000, XP002306735, Database Accession No. AA416682.
Database EMBL, Mar. 3, 2000, XP002306736, Database Accession No. AA416577.
Database EMBL, Dec. 1, 2001, XP002306737, Database Accession No. Q96P76.
Database EMBL, Oct. 15, 2001, XP002306738, Database Accession No. AF407333.
Database EMBL, Dec. 1, 2001, XP002306739, Database Accession No. Q91ZR5.
Database EMBL, Oct. 15, 2001, XP002306740, Database Accession No. AF407332.
Ren et al., A Sperm Ion Channel Required for Sperm Motility and Male Fertility, Nature, Macmillian Journals Ltd., London, vol. 413, No. 6856, Oct. 11, 2001, pp. 603-609.
Database EMBL, Oct. 20, 2000, XP002314898, Database Accession No. BF092492.
Database EMBL, Oct. 8, 2001, XP002314906, Database Accession No. BI826910.
Database EMBL, Oct. 8, 2001, XP002314907, Database Accession No. BI829451.
Database EMBL, May 9, 2001, XP002314908, Database Accession No. BG718343.
Database EMBL, May 9, 2001, XP002314909, Database Accession No. BG718245.
Database EMBL, Nov. 29, 2001, XP002314910, Database Accession No. ABL90376.
Database EMBL, Nov. 29, 2001, XP002314911, Database Accession No. ABB89967.

(Continued)

*Primary Examiner* — Gary Nickol
*Assistant Examiner* — Sandra Wegert
(74) *Attorney, Agent, or Firm* — Wilmer Cutler Pickering Hale and Dorr LLP

(57) ABSTRACT

Nucleic acid and protein sequences relating to a cation channel which is sperm-specific (CatSper1) are disclosed. The CatSper1 protein is shown to be specifically expressed in sperm and to be necessary for sperm motility. Nucleic acids, vectors, transformed cells, transgenic animals, polypeptides, and antibodies relating to the CatSper1 gene and protein are disclosed. Also provided are methods of in vitro fertilization and contraception, methods of identifying modulators of CatSper1 activity, methods of genotyping subjects with respect to CatSper1, and methods of diagnosing and treating CatSper1-mediated disorders, including infertility.

22 Claims, 5 Drawing Sheets

OTHER PUBLICATIONS

Database EMBL, Mar. 25, 2004, XP002314912, Database Accession No. ACN41330.
Database EMBL, Jan. 25, 2001, XP002314968, Database Accession No. BF934163.
Garbers D.L., "Ion channels. Swimming with sperm," Nature, vol. 413, No. 6856, Oct. 2001, pp. 579, 581-582, XP 002314956.
Quill, T. A., et al., "A voltage-gated ion channel expressed specifically in spermatozoa," Proc. Natl. Acad. Sci. USA, vol. 98, No. 22, Oct. 2001, pp. 12527-12531, XP002253116.
Database EMBL, Jun. 8, 2000, XP002314899, Database Accession No. AW971983.
Database EMBL, Nov. 14, 1997, XP002314900, Database Accession No. AA662668.
Database EMBL, Dec. 2, 2000, XP002314901, Database Accession No. BF436942.
Database EMBL, Sep. 11, 1997, XP002314902, Database Accession No. AA574312.
Database EMBL, Nov. 30, 1999, XP002314903, Database Accession No. AW197851.
Database EMBL, Mar. 2, 2000, XP002314904, Database Accession No. AW472972.
Database EMBL, Oct. 11, 2001, XP002314905, Database Accession No. AAS90759.
Avidan et al., European Journal of Human Genetics, 2003, 11:497-502.
Lobley et al., Reprod. Biol. Endocrinol. 2003, 1:53, 15 pages.
Skolnick et al., Trends in Biotechnology, 2000, 18: 34-39.
Whisstock et al., Quarterly Review of Biophysics, 2003, 36:307-340.
Amoult, et al., "Activation of mouse sperm T-type Ca2+ channels by adhesion to the egg zona pellucida," Proc. Natl. Acad. Sci. USA, vol. 93, pp. 13004-13009, 1996.
Bedford, J.M., "Mammalian Fertilization Misread? Sperm Penetration of the Eutherian Zona Pellucida Is Unlikely to be a Lytic Event," Biology of Reproduction, vol. 59, pp. 1275-1287, 2000.
Darszon, et al., "Ion Channels in Sperm Physiology," Physiological Reviews, vol. 79, No. 2, Apr. 1999, pp. 481-510.
Hyne and Gaiters, "Calcium-dependent increase in adenosine 3', 5'-monophosphate and induction of the acrosome reaction in guinea pig spermatozoa," Proc. Natl. Acad. Sci. USA, vol. 76, No. 11, pp. 5699-5703, 1999.
Jungnickel, et al., "Trp2 regulates entry of Ca2+ into mouse sperm triggered by egg ZP3," Nature Cell Biology, vol. 3, May 2001, pp. 499-502.
O'Toole, et al., "Ca2+ Entry through Store-operated Channels in Mouse Sperm Is Initiated by Egg ZP3 and Drives the Acrosome Reaction," Molecular Biology of the Cell, vol. 11, pp. 1571-1584, May 2000.
Quill, et al., "A voltage-gated ion channel expressed specifically in spermatozoa," PNAS, vol. 98, No. 22, 12527-12531, 2000.
Santi, et al., "A dihydropyridine-sensitive T-type Ca2+ current is the main Ca2+ current carrier in mouse primary spermatocytes," American Journal of Physiology, vol. 271, pp. C1583-C1593, 1996.
Serrano, et al., "Voltage-dependent Ca2+ channel subunit expression and immunolocalization in mouse spermatogenic cells and sperm," FEBS Letters, 462, pp. 171-176, 1999.
Database NCBI, Accession No. BC047442, Strausberg, R., *Homo sapiens*, Clone Image. Mar. 3, 2003, pp. 1-3, especially pp. 2-3.
Tash, Joseph S., "Role of the Camp, Calcium, and Protein Phosporylation in Sperm Motility," Controls of Sperm Motility: Biological and Clinical Aspects, eds. Gagnon, pp. 229-240, 1990.
Wassarman, et al., "A profile of fertilization in mammals," Nature Cell Biology, vol. 3, E59-E64, Feb. 2001.
Weyand, et al., "Cloning and functional expression of a cyclic nucleotide-gated channel from mammalian sperm," Nature, vol. 368, pp. 859-863, Apr. 28, 1994.
Wennemuth, et al., "Cav2.2 and Cav2.3 (N- and R-type) Ca2+ Channels in Depolarization-evoked Entry of Ca2+ into Mouse Sperm," The Journal of Biological Chemistry, vol. 275, No. 28, pp. 21210-21217, 2000.
Wiesner, et al., "Cyclic Nucleotide-gated Channels on the Flagellum Control of Ca2+ Entry into Sperm," The Journal of Cell Biology, vol. 142, No. 2, pp. 473-484, 1998.
Yanigimachi, R. "Mammalian Fertilization," The Physiology of Reproduction, Second Edition, eds. Knobil and Neill, pp. 189-317, 1994.
Chan H.C., Cation and anion channels in rat and human spermatozoa, Biochimica et Biophysica Acta, vol. 1323; pp. 117-129 (1997).
Colman, P.M., "Effects of amino acid sequence changes on antibody-antigen interactions," Research in Immunology, vol. 145; pp. 33-36 (1994).
Database EMBL, May 9, 2001, XP002314909, Database Accession No. BG718245; 2 pages.
Jin et al., "Catsper3 and Catsper4 encode two cation channel-like proteins exclusively expressedmin the testis," Biology of Reproduction, vol. 73, pp. 1235-1242 (2005).
Martelange et al., "Identification on a Human Sarcoma of two new genes with tumor-specific expression," Cancer Research, vol. 60, pp. 3848-3855 (2000).
Watson et al., Recombinant DNA, 2nd Edition, W.H. Freeman and Company, p. 107, (1992).

* cited by examiner

MDQSSRRDESYHETHPGSLDPSHQSHPHPHPTLHRPNQGGVYYDSPQH 50
GMFQQPYQQHGGFHQQNELQHLREFSDSHDNAFSHHSYQQDRAGVSTLPN 100
NISHAYGGSHPLAESQHSGGPQSGPRIDPNHHPHQDDPHRPSEPLSHPSS 150
TGSHQGTTHQQYHERSHHLNPQQNRDHADTISYRSSTRFYRSHAPFSRQE 200
RPHLHADHHHEGHHAHSHHGEHPHHKEQRHYHGDHMHHHIHHRSPSASQL 250
SHKSHSTLATSPSHVGSKSTASGARYTFGARSQIFGKAQSRESLRESASL 300
SEGEDHVQKRKKAQRAHKKAHTGNIFQLLWEKISHLLLGLQQMILSLTQS 350
<u>LGFETFIFIVVCLNTVILVAQT</u>FTELEIRGEWYF<u>MVLDSIFLSIYVLEAV</u> 400
    S1                                                    S2
<u>LKLIAL</u>GLEYFYDPWNNLD<u>FFIMVAVLDFVLLQINSL</u>SYSFYNHSL<u>FRI</u> 450
  S4                                       S5
<u>LKVFKSMRALRAIRVLRRL</u>SILTSLHEVAGTLSGSLPS<u>ITAILTLMFTCL</u> 500
                                    P
<u>FLFSVVLRAL</u>FQDSDPKRFQ<u>NIFTTLFTLFTMLTLDDWSLIY</u>IDNRAQGA 550
   S6
WYIIPILMIYIVIQYFIFLNLVIAVLVDNFQMALLKGLEKVKLEQAARVH 600
EKLLDDSLTDLNKADANAQMTEEALKMQLIEGMFGNMTVQRVLHFQFLQ 650
LVAAVEQHQQKFRSQAYVIDELVDMAFEAGDDDYGK 686

FIG. 1A

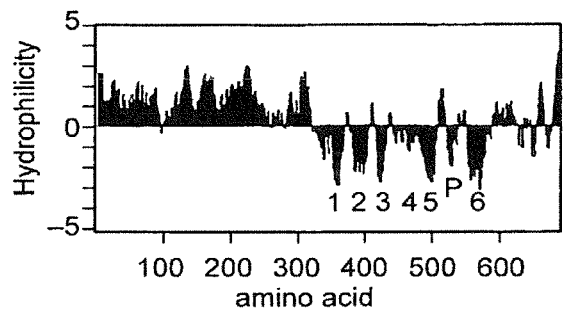

FIG. 1B

Pore region

```
            CatSper   RFQNIFTTLFTLFTMLTLDDWSLIYID
            Cav1.2    NFDNFAFAMLTVFQCITMEGWTDVLYN
    I       Cav2.2    NFDNILFAILTVFQCITMEGWTDILYN
            Cav3.1    NFDNIGYAWIAIFQVITLEGWVDIMYF
            Cav1.2    TFDNFPQSLLTVFQILTGEDWNSVMYD
    II      Cav2.2    NFDTFPAAILTVFQILTGEDWNAVMYN
            Cav3.1    NFDSLLWAIVTVFQILTQEDWNKVLYN
            Cav1.2    DFDNVLAAMMALFTVSTFEGWPELLYR
    III     Cav2.2    HYDNVLWALLTLFTVSTGEGWPMYLKH
            Cav3.1    NFDNLGQALMSLFVLASKDGWVDIMYD
            Cav1.2    NFQTFPQAVLLLPRCATGEAWQDIMLA
    IV      Cav2.2    NFRTFLQALMLLFRSATGEAWHEIMLS
            Cav3.1    TFRNFGMAFLTLFRVSTGDNWNGIMKD
```

FIG. 1C

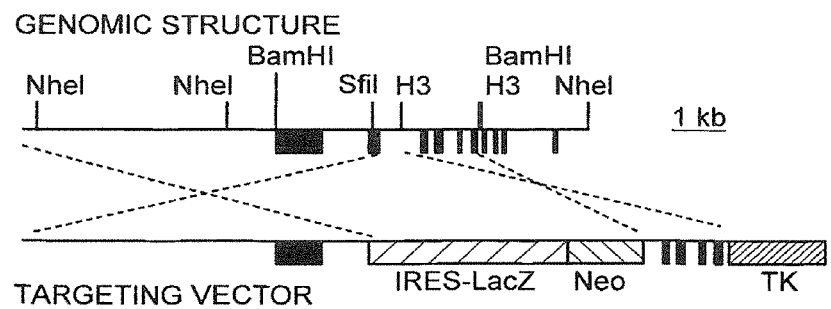

FIG. 2

SPERM-SPECIFIC CATION CHANNEL, CATSPER1, AND USES THEREFOR

RELATED APPLICATIONS

This application claims benefit of priority to U.S. Provisional Patent Appln. Ser. No. 60/288,402, filed May 3, 2001, U.S. Provisional Patent Appln. Ser. No. 60/327,167, filed Oct. 4, 2001 and PCT International Application No. PCT/US02/13847 filed May 3, 2002.

SEQUENCE LISTING

The instant application contains a Sequence Listing which has been submitted in ASCII format via EFS-Web and is hereby incorporated by reference in its entirety. Said ASCII copy, created on Dec. 29, 2011, is named 110313US.txt and is 25 kilobytes in size.

BACKGROUND OF THE INVENTION

1. Field of the Invention

The present invention relates to the fields of molecular biology, and reproductive technology. In particular, the invention relates to a cation channel protein expressed specifically in sperm cells, to nucleic acids encoding the protein, cells engineered to express the protein, assays for compounds affecting the activity of the protein, and to the use of such compounds in the treatment or causation of infertility, or as a means of contraception or animal control.

2. Description of the Related Art

Sperm and ova reciprocally interact in mammalian fertilization (Wassarman, et al. (2001), *Nature Cell Biology* 3, E59-E64; Yanagimachi (1994), in *The Physiology of Reproduction*, eds. Knobil & Neill (Raven Press, New York), pp. 189-315). To reach the site of fertilization, sperm must travel relatively long distances and become primed for fertilization of the ova through capacitation and other processes. Once they arrive at the surface of an ovum, sperm interact with ovum extracellular matrix glycoproteins including the zona pellucida proteins. Sperm release acidic material during the acrosome reaction, a signaling event that presumably involves the opening of $Ca^{2+}$ channels and the influx of $Ca^{2+}$ into the sperm heads (O'Toole, et al. (2000), *Mol Biol Cell* 11, 1571-84). The TRPC2 protein, a putative $Ca^{2+}$-permeant channel, has recently been implicated in the acrosome reaction (Jungnickel, et al. (2001), *Nat Cell Biol* 3, 499-502). Penetration of sperm through the thick outer layer of the ovum is achieved through chemical lysis of the ovum coat and/or the mechanical motion of sperm (Bedford (1998), *Biol Reprod* 59, 1275-87). Following infiltration of the ovum ZP coat, the sperm membrane fuses with that of ovum. Fusion is followed by activation of the fertilization process, beginning with $Ca^{2+}$ oscillations in the ovum (Wassarman, et al. (2001), *Nature Cell Biology* 3, E59-E64; Yanagimachi (1994), in *The Physiology of Reproduction*, eds. Knobil & Neill (Raven Press, New York), pp. 189-315).

$Ca^{2+}$ and cyclic nucleotides control sperm motility (Tash (1990) in *Controls of Sperm Motility: biological and clinical aspects*, ed. Gagnon (CRC Press, Boca Raton), pp. 229-240; Darszon, et al. (1999), *Physiol Rev* 79, 481-510; Hyne & Garbers (1979), *Proc Natl Acad Sci USA* 76, 5699-703) and several voltage-dependent $Ca^{2+}$ channel ($Ca_V$) mRNAs and cyclic nucleotide-gated (CNG) channel proteins have been detected in sperm cell precursors (Darszon, et al. (1999), *Physiol Rev* 79, 481-510; Serrano, et al. (1999), *FEBS Lett* 462, 171-6; Weyand, et al. (1994) *Nature* 368, 859-63; Wiesner, et al. (1998), *J Cell Biol* 142, 473-84). Furthermore, low voltage activated, dihydropyridine-sensitive "T-type" channels (Santi, et al. (1996), *Am J Physiol* 271, C1583-93; Arnoult, et al. (1996), *Proc Natl Acad Sci USA* 93, 13004-9) and pharmacologically defined N- and R-type currents have been measured in spermatogenic cells (Wennemuth, et al. (2000), *J Biol Chem* 275, 21210-7). But the role of these channels in spermatogenesis or mature sperm function is not known.

SUMMARY OF THE INVENTION

In one aspect, the present invention provides isolated nucleic acids corresponding to all or a portion of a CatSper1 gene. In some embodiments, the isolated nucleic acids include a nucleotide sequence of at least 10, 12, 14, 16 or 18 consecutive nucleotides of SEQ ID NO: 1 or SEQ ID NO: 3, or a sequence complementary thereto. In other embodiments, the nucleic acids include nucleotide sequences encoding a CatSper1 protein, at least a transmembrane domain of a CatSper1 protein, at least an extracellular loop of a CatSper1 protein, at least a pore region of a CatSper1 protein, at least an epitope of a CatSper1 protein having high predicted antigenicity, or a sequence complementary thereto. In particular embodiments, the nucleic acids include a sequence of SEQ ID NO: 1; a sequence of SEQ ID NO: 3; a sequence encoding a polypeptide comprising residues 447-468, 481-502, 516-533, 542-563, 583-604 or 649-670 of SEQ ID NO: 2; a sequence encoding a polypeptide comprising residues 351-372, 385-406, 419-438, 448-469, 489-510, or 555-576 of SEQ ID NO: 4; a sequence encoding a polypeptide comprising residues 469-480, 534-541, or 605-648 of SEQ ID NO: 2; a sequence encoding a polypeptide comprising residues 373-384, 439-448, and 511-554 of SEQ ID NO 4; a sequence encoding a polypeptide comprising residues 616-635 of SEQ ID NO: 2; a sequence encoding a polypeptide comprising residues approximately residues 522-541 of SEQ ID NO: 4; a sequence encoding a polypeptide comprising residues 2-34, 52-70, 108-130, 264-305, 387-417, or 606-614 of SEQ ID NO: 2; a sequence encoding a polypeptide comprising residues 2-40, 120-148, 160-200, or 512-520 of SEQ ID NO: 4; and a sequence complementary thereto.

In another aspect, the invention provides isolated nucleic acids encoding polypeptide having at least 80%, 85%, 90%, or 95% amino acid sequence identity with a CatSper1 protein; at least a transmembrane domain of a CatSper1 protein; at least an extracellular loop of a CatSper1 protein; and at least a pore region of a CatSper1 protein. In some embodiments, the isolated nucleic acids encode a polypeptide having at least 80%, 85%, 90% or 95% amino acid sequence identity with a CatSper1 protein and having CatSper1 activity in a cell capable of expressing CatSper1 activity. In some embodiments, the isolated nucleic acids include a regulatory element having at least 80%, 85%, 90% or 95% nucleotide sequence identity to at least 100, 200, 300 or 400 consecutive nucleotides from SEQ ID NO: 5, and that is capable of promoting transcription of a coding sequence operably joined thereto in a mammalian cell in which a CatSper1 gene can be expressed.

In another aspect, the invention provides isolated nucleic acids that hybridize to at least a portion of a nucleic acid of SEQ ID NO: 1 or SEQ ID NO: 3 under conditions including a wash step of 1.0×SSC at 65° C., a wash step of 0.5×SSC, a wash step of 0.2×SSC, or a wash step of 0.1×SSC. In some embodiments, the isolated nucleic acids encode a polypeptide having CatSper1 activity.

In another aspect, the invention provides nucleic acid comprising a nucleotide sequence encoding a polypeptide having CatSper1 activity, and that hybridizes to at least a portion of a nucleic acid of SEQ ID NO: 1 or SEQ ID NO: 3 under conditions including a wash step of 1.0×SSC at 65° C., a wash step of 0.5×SSC, a wash step of 0.2×SSC, or a wash step of 0.1×SSC; and that is operably joined to a heterologous regulatory region such that the sequence is expressed. In another embodiment, the invention provides a nucleic acid comprising a nucleotide sequence encoding a polypeptide having at least 80%, 85%, 90% or 95% amino acid sequence identity with an amino acid sequence of SEQ ID NO: 2 or 4; and is operably joined to a heterologous regulatory region such that the sequence is expressed.

In another aspect, the invention provides a kit for detecting at least a portion of a CatSper1 nucleic acid. The kits can include any of the foregoing isolated nucleic acids of the invention, and a means for detecting the isolated nucleic acid. In some embodiments, the means for detecting the isolated nucleic acid includes a detectable label bound thereto and, in some embodiments, the means includes a labeled secondary nucleic acid which specifically hybridizes to the first isolated nucleic acid.

In another aspect, the invention provides vector including any of the foregoing isolated nucleic acids of the invention. In some embodiments, the vector includes a genetic construct capable of expressing the nucleic acids of the invention. In some embodiments, the nucleic acids of the invention are operably joined to an exogenous regulatory region and, in some embodiments, the nucleic acids are operably joined to heterologous coding sequences to form a fusion vector. In some embodiments, the vector includes a CatSper1 regulatory region and, in some embodiments, the CatSper1 regulatory region is operably joined to a heterologous coding sequence.

In another aspect, the invention provides cells transformed with the foregoing nucleic acids of the invention, or a genetic construct capable of expressing a nucleic acid of the invention. In some embodiments, the nucleic acid of the invention is operably joined to heterologous coding sequences to encode a fusion protein. In some embodiments, the cells are bacterial cells, yeast cells, insect cells, nematode cells, amphibian cells, rodent cells, or human cells. In some embodiments, the cells are mammalian somatic cells, fetal cells, embryonic stem cells, zygotes, gametes, germ line cells and transgenic animal cells.

In another aspect, the invention provides non-human transgenic animals. In these aspects, a genetic construct has introduced a modification into a genome of the animal, or an ancestor of the animal, and the modification includes insertion of a nucleic acid encoding at least a fragment of a CatSper1 protein, inactivation of an endogenous CatSper1 gene, or insertion by homologous recombination of a reporter gene operably joined to CatSper1 regulatory elements. In some embodiments, the modification is insertion of nucleic acid encoding a CatSper1 protein, at least a transmembrane domain of a CatSper1 protein, at least an extracellular loop of a CatSper1 protein, at least a pore region of a CatSper1 protein, or at least an epitope of a CatSper1 protein having high predicted antigenicity. In some embodiments, the animals are rats, mice, hamsters, guinea pigs, rabbit, dogs, cats, goats, sheep, pigs, and non-human primates.

In another aspect, the invention provides substantially pure protein preparations including polypeptides selected from a CatSper1 protein; at least a transmembrane domain of a CatSper1 protein; at least an extracellular loop of a CatSper1 protein; at least a pore region of a CatSper1 protein; and at least an epitope of a CatSper1 protein having high predicted antigenicity. In particular embodiments, the polypeptide is selected from SEQ ID NO: 2; SEQ ID NO: 4; residues 447-468, 481-502, 516-533, 542-563, 583-604 or 649-670 of SEQ ID NO: 2; residues 351-372, 385-406, 419-438, 448-469, 489-510, or 555-576 of SEQ ID NO: 4; residues 469-480, 534-541, or 605-648 of SEQ ID NO: 2; residues 373-384, 439-448, and 511-554 of SEQ ID NO 4; residues 616-635 of SEQ ID NO: 2; residues 522-541 of SEQ ID NO: 4; residues 2-34, 52-70, 108-130, 264-305, 387-417, or 606-614 of SEQ ID NO: 2; and residues 2-40, 120-148, 160-200, or 512-520 of SEQ ID NO: 4.

In another aspect, the invention provides a substantially pure protein preparation including polypeptides having at least 80%, 85%, 90%, or 95% amino acid sequence identity with a CatSper1 protein; at least a transmembrane domain of a CatSper1 protein; at least an extracellular loop of a CatSper1 protein; or at least a pore region of a CatSper1 protein. In some embodiments, the substantially pure protein preparation includes a polypeptide having at least 80%, 85%, 90%, or 95% amino acid sequence identity with a CatSper1 protein and having CatSper1 activity in a cell capable of expressing CatSper1 activity.

In another aspect, the invention provides a substantially pure antibody preparation including an antibody raised against a CatSper1 epitope. In some embodiments, the epitope has high predicted antigenicity. In some embodiments, the epitope includes an amino acid sequence within residues 2-34, 52-70, 108-130, 264-305, 387-417, and 606-614 of SEQ ID NO: 2, and residues 2-40, 120-148, 160-200, or 512-520 of SEQ ID NO: 4. In some embodiments, the antibody is a monoclonal antibody. In some embodiments, antibody is an Fab fragment, an F(ab')$_2$ fragment, an Fv fragment, or a single-chain Fv fragment (scFv).

In another aspect, the invention provides a kit for detecting at least an epitope of a CatSper1 protein. The kits include an anti-CatSper1 antibody of the invention and a means for detecting said antibody. In some embodiments, the means for detecting said anti-CatSper1 antibody includes a detectable label bound thereto and, in some embodiments, the means for detecting said anti-CatSper1 antibody includes a labeled secondary antibody which specifically binds to the anti-CatSper1 antibody.

In another aspect, the invention provides methods of identifying potential modulators of CatSper1 activity. The methods include contacting a candidate compound with a cell expressing a CatSper1 protein; measuring an indicator of CatSper1 activity in the cell; determining whether the candidate compound caused an increase or decrease in the indicator relative to a reference level; and identifying the candidate compound as a potential modulator of CatSper1 activity if the increase or decrease is significant. In some embodiments, the indicator is an indicator of the level of mRNA encoding the CatSper1 protein, an indicator of the level of CatSper1 protein, an indicator of cation flux across a membrane of said cell, or an indicator of whole cell or channel currents of said cell. In some embodiments, the cell has been transformed with a genetic construct capable of expressing a CatSper1 protein. In some embodiments, the cell is a mature sperm cell and the indicator is a measure of sperm motility.

In another aspect, the invention provides methods of identifying a potential modulator of CatSper1 activity comprising contacting a candidate compound with at least a structural domain of a CatSper1 protein; measuring binding, if any, between the candidate compound and the CatSper1 moiety; and identifying the candidate compound as a potential modulator of CatSper1 activity if the binding is significant. In some embodiments, the CatSper1 moiety is a CatSper1 protein; at least a transmembrane domain of a CatSper1 protein; at least an extracellular loop of a CatSper1 protein; or at least a pore region of a CatSper1 protein.

In another aspect, the invention provides a method of decreasing the fertility of a male subject by administering a compound to the subject which decreases CatSper1 activity. In another aspect, the invention provides a method of causing reversible infertility in a male subject by administering to a compound to the subject which decreases CatSper1 activity. In another aspect, the invention provides a method of contraception in which a compound which decreases CatSper1 activity is administered to a male or female subject. In each of the foregoing embodiments, the compound can be in an injection, a transdermal patch, a bioerodable implant, a lubricant, a moisturizer, a foam, a jelly, or a sponge. If the subject is a female, the compound can be administered into at least one of the vagina, uterus or fallopian tubes. In each of the foregoing embodiments, the compound can be a nucleic acid which is anti sense to at least a portion of a CatSper1 gene or an antibody to a CatSper1 protein, including an Fab fragment, an F(ab')$_2$ fragment, an Fv fragment, or an scFv fragment. In some embodiments, the subject is a mammal. In some embodiments, the subjects are humans, dogs, cats, cows, sheep, horses, mice, rats, raccoons, and gophers. In others embodiments, the subjects are fish, amphibians or insects. In related aspects, the invention provides for the use of a compound which decreases CatSper1 activity in the preparation of a medicament for decreasing the fertility of a male subject, or causing reversible infertility in a male subject, or in the preparation of a contraceptive for administration to a male or female. thus, the invention provides contraceptive preparations including compounds which decrease CatSper1 activity, including nucleic acids which are antisense to at least a portion of a CatSper1 gene and antibodies to a CatSper1 protein.

In another aspect, the invention provides method of diagnosing a CatSper1-related disorder in a mammal by determining the presence or absence of a mutation in a CatSper1 gene. In some embodiments, the presence or absence of differences between a determined nucleic acid or amino acid sequence and a reference sequence indicates the presence or absence of mutations in the CatSper1 gene. In some embodiments, the method includes contacting at least a fragment of the CatSper1 protein with an antibody known to bind to a CatSper1 protein in which a mutation is known to be present or absent and detecting binding between the antibody and the CatSper1 protein. In other embodiments, the method includes measuring an indicator of CatSper1 activity in a cell; and comparing the measured indicator to a reference level. The indicator can be an indicator of the level of mRNA encoding CatSper1 protein, an indicator of the level of CatSper1 protein, an indicator of cation flux across a membrane of said cell, or an indicator of whole cell or channel currents of said cell. In some embodiments, the disorder is CatSper1-related infertility. In another aspect, the invention provides methods of genotyping a subject with respect to a CatSper1 gene.

In another aspect, the invention provides a method of in vitro fertilization by sperm having decreased CatSper1 activity, decreased motility, or decreased ability to penetrate a zona pellucida, in which a zona pellucida is removed from at least one ovum; and the ovum is contacted with at least one of sperm.

In another aspect, a method of treating a subject characterized by infertility due to decreased CatSper1 activity is provided. The method includes transforming sperm or sperm progenitors of the subject with a genetic construct capable of expressing a CatSper1 protein and using transformed sperm of said subject to fertilize an ovum. Alternatively, the method includes administering a CatSper1 protein to sperm or sperm progenitors of the subject.

In another aspect, the invention provides methods of diagnosing an anti-CatSper1 antibody-mediated infertility caused by anti-CatSper1 antibodies present in a female urogenital tract is provided. In another aspect, methods of treating an anti-CatSper1 antibody-mediated infertility caused by anti-CatSper1 antibodies present in a female urogenital tract are provided.

BRIEF DESCRIPTION OF THE DRAWINGS

The following drawings are illustrative of embodiments of the invention and are not meant to limit the scope of the invention.

DETAILED DESCRIPTION

Figure 3A:
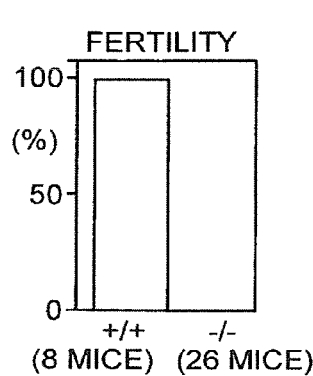
FIG. 3 shows male infertility caused by CatSper1 disruption. (a) Fertility of CatSper1$^{+/+}$ and CatSper1$^{-/-}$ males. Mice body and testis weight (b) and sperm count (c) were not significantly different. (d) $Ca^{2+}$ channel currents were indistinguishable between +/+ and −/− mice in range of activation, amplitude and kinetics. Currents elicited by test pulses from −90 to +20 mV (±10 mV). Lower panel; averaged I/V relations of inward currents. Holding potential=−100 mV. Average cell capacitance was 10.8±1.4 pF (n=9, +/+) and 12.9±0.9 pF (n=11, −/−).

The present invention depends, in part, upon the identification, isolation and characterization of a cation channel protein which is expressed in sperm cells, but not in other tissues tested, and which plays a significant role in the motility of sperm and their ability to fertilize ova. The protein has been designated CatSper1 to indicate that it is the first Cation channel which is Sperm-specific to be identified. Significantly, inhibition of the activity of CatSper1 causes a substantial decrease in the motility of sperm cells, particularly the most vigorous sperm tail beating required for penetration of the zona pellucida (ZP) and subsequent fertilization. Therefore, inhibitors of the activity of the CatSper1 protein can prevent penetration of the ZP and can be used as male and female contraceptives.

The CatSper1 gene is unique in that it encodes a single 6 transmembrane-spanning repeat (similar to voltage-dependent $K^+$ [$K_V$] channels), while its pore region and overall homology closely resemble a single domain of the much larger four repeat $Ca^{2+}$ channels ($Ca_V$). The gene product is exclusively expressed in the testis and not in other tissues such as the brain, heart, kidney or the immune system. In sperm, the channel is localized primarily to the tail's principal piece, not the head or midpiece. As shown in the examples below, poor sperm motility and male infertility result from gene-targeted elimination of the mouse CatSper1 protein.

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference. In particular, the entire disclosures of U.S. Provisional Patent Appln. Ser. No. 60/288,402 and U.S. Provisional Patent Appln. Ser. No. 60/327,167 are incorporated herein by reference.

DEFINITIONS

All technical and scientific terms used herein, unless otherwise defined below, are intended to have the same meaning as commonly understood by one of ordinary skill in the art; references to techniques employed herein are intended to refer to the techniques as commonly understood in the art, including variations on those techniques or substitutions of equivalent techniques which would be apparent to one of skill in the art. In order to more clearly and concisely describe the subject matter which is the invention, the following definitions are provided for certain terms which are used in the specification.

As used herein, the term "CatSper1 protein" means a sperm-specific cation channels such as the human CatSper1 protein disclosed in SEQ ID NO: 2, human allelic variants of the disclosed CatSper1 protein, mammalian homologs of these human CatSper1 proteins, and functional equivalents thereof. The term CatSper1 protein refers to naturally occurring proteins as isolated from sperm, recombinantly produced proteins from cells transformed with CatSper1 genes, and fusion proteins in which CatSper1 sequences are fused to N-terminal or C-terminal polypeptides. The term "fragment" refers to fragments of the CatSper1 proteins, such as structural domains and epitopes. A fragment of a CatSper1 protein comprises at least six amino acid residues.

As used herein, the term "CatSper1 gene" means a gene encoding a CatSper1 protein, including the human CatSper1 protein disclosed in SEQ ID NO: 2, human allelic variants of the disclosed CatSper1 protein, mammalian homologs of these human CatSper1 proteins, and functional equivalents thereof. The term CatSper1 gene refers to both naturally occurring genes as isolated from genomic DNA, and recombinantly produced genes in which the CatSper1 coding regions are operably joined to either endogenous or exogenous regulatory elements, with or without intron sequences, and with or without 5' or 3'-flanking sequences which may encode heterologous (i.e., non-CatSper1) sequences to form a CatSper1 fusion protein. A CatSper1 gene will include, at a minimum, a coding region encoding the protein operably joined to regulatory elements (e.g., promoters, enhancer) which allow transcription of the coding region to mRNA which can be translated into a CatSper1 protein.

As used herein "CatSper1" activity means any normal biological activity of a wild-type CatSper1 protein when expressed in a cell or cell type in which CatSper1 is normally expressed and under conditions under which CatSper1 is normally expressed. Such activity may include induction of an ion current; mediation of cAMP-induced Ca influx; restoration of sperm motility when expressed in CatSper1 −/− sperm; and/or restoration of the ability to penetrate eggs when expressed in CatSper1 −/− sperm. CatSper1 activity can be measured in sperm cells or spermatocytes, or in other cells in which any necessary accessory factors are present.

As used herein with respect to nucleic acid and amino acid sequences, the term "identity" means a measure of the degree of similarity of two sequences based upon an alignment of the sequences which maximizes identity and which is a function of the number of identical nucleotides or residues, the number of total nucleotides or residues, and the presence and length of gaps in the sequence alignment. A variety of algorithms and computer programs are available for determining sequence identity using standard parameters. For example, Gapped BLAST or PSI-BLAST (Altschul et al. (1997), Nucleic Acids Res. 25:33 89-3402), BLAST (Altschul et al. (1990) J. Mol. Biol. 215:403-410), and Smith-Waterman (Smith et al. (1981), J. Mol. Biol. 147:195-197). As used herein, percent identity is based upon the default values for the BLAST algorithms.

As used herein, the term "homolog" means a protein which is evolutionarily-related to and shares substantial, conserved structural and functional similarity with a reference protein, but which is present in a different species (e.g., human, rat, and insect CatSper1 proteins are homologs of each other).

As used herein, the term "mutation" refers to a change in a nucleic acid sequence, whether or not expressed as a change in a corresponding encoded protein sequence, relative to some reference sequence. The reference sequence may be a "wild-type" sequence (i.e., one or more high frequency sequences in a population corresponding to a "normal" phenotype), or any other sequence. As used herein, the term mutation is intended to be synonymous with the term polymorphism, and therefore the differences between any two non-identical sequences may be regarding as mutations. The term mutation is intended to encompass insertions, deletions and/or substitutions of one or more nucleotides relative to a reference sequence.

As used herein, the terms "exogenous" or "heterologous" mean, with respect to two or more genetic sequences, that the genetic sequences do not occur in the sane physical relation to each other in nature and/or do not naturally occur within the same genome. For example, a genetic construct may include a coding region which is operably joined to one or more regulatory elements, and these sequences are considered heterologous to each other if they are not operably joined in nature and/or they are not found in the same genome in nature. Similarly, a genetic construct which is introduced into a cell is considered heterologous to that cell to the extent that it contains genetic sequences not found in that cell. In addition, a synthetically-produced genetic sequence based upon a naturally occurring sequence, will be heterologous to the naturally-occurring sequence to the extent codons have been altered and the synthetic sequence does not exist in nature. Allelic variants of a sequence in a species are not considered heterologous to each other.

As used herein, the term "operably joined" refers to a covalent and functional linkage of genetic regulatory elements and a genetic coding region which can cause the coding region to be transcribed into mRNA by an RNA polymerase which can bind to one or more of the regulatory elements. Thus, a regulatory region, including regulatory elements, is operably joined to a coding region when RNA polymerase is capable under permissive conditions of binding to a promoter within the regulatory region and causing transcription of the coding region into mRNA. In this context, permissive conditions would include standard intracellular conditions for constitutive promoters, standard conditions and the absence of a repressor or the presence of an inducer for repressible/inducible promoters, and appropriate in vitro conditions, as known in the art, for in vitro transcription systems.

As used herein, the term "expression" refers to the process by which a coding sequence of a gene is transcribed into a primary mRNA transcript, the primary mRNA transcript is processed into a mature mRNA, and the mature mRNA is translated into a protein. Expression may optionally include post-translation modifications of the resulting polypeptide.

As used herein, the phrase "genetic construct encoding a CatSper1 protein" means a recombinant DNA, RNA, or nucleic acid analog molecule which includes a genetic sequence encoding, or which is complementary to a genetic sequence encoding, the amino acid sequence of the CatSper1 protein, and which is capable of being expressed in a cell which has been transformed with the construct. The construct may express the CatSper1 protein transiently, or may stably integrate into the genome of the cell and express the protein conditionally or constitutively.

As used herein, the term "vector" means any genetic construct, such as a plasmid, phage, transposon, cosmid, chromosome, virus, virion, etc., which is capable transferring gene sequences between cells. Vectors may be capable of one or more of replication, expression, and insertion or integration, but need not possess each of these capabilities. Thus, the term includes cloning, expression, homologous recombination, and knock-out vectors.

As used herein, with respect to genetic engineering, the term "transform" means to introduce into a cell or an organism an exogenous nucleic acid or nucleic acid analog which replicates within that cell or organism, that encodes a polypeptide sequence which is expressed in that cell or organism, and/or that is integrated into the genome of that cell or organism so as to affect the expression of a genetic locus. The term "transform" is used to embrace all of the various methods of introducing such nucleic acids or nucleic acid analogs, including, but not limited to the methods referred to in the art as transformation, transfection, transduction, electroporation, ballistic injection, and the like.

As used herein, a "nucleic acid analog" means a molecule having sufficient structural and functional similarity to a nucleic acid to direct sequence-specific forward or reverse transcription of complementary nucleic acids, or to direct sequence-specific translation of an encoded polypeptide within a living cell.

As used herein, the term "reporter gene" means any genetic sequence which, when expressed, has a biochemical or phenotypic effect which is detectable. Reporter genes are also known in the art as "marker" genes.

As used herein, the term "antibody" is intended to embrace naturally produced antibodies, recombinantly produced antibodies, and antibody fragments such as Fab fragments, F(ab')$_2$ fragments, Fv fragments, and single-chain Fv fragment (scFv).

As used herein, the term "effective amount" of an agonist or antagonist, or an enhancer or repressor, means the total amount of the active component(s) of a composition that is sufficient to cause a statistically significant change on a detectable biochemical or phenotypic characteristic. When applied to an individual active ingredient, administered alone, the term refers to that ingredient alone. When applied to a combination, the term refers to combined amounts of the active ingredients that result in the effect, whether administered in combination, serially or simultaneously.

As used herein, the term "substantially pure" means a preparation which contains at least 60% (by dry weight) of the protein of interest, exclusive of the weight of other intentionally included compounds. Preferably the preparation is at least 75%, more preferably at least 90%, and most preferably at least 99%, by dry weight of the protein of interest, exclusive of the weight of other intentionally included compounds. Purity can be measured by any appropriate method, e.g., column chromatography, gel electrophoresis, amino acid compositional analysis or HPLC analysis. If a preparation intentionally includes two or more different proteins of the invention, a "substantially pure" preparation means a preparation in which the total dry weight of the protein of the invention is at least 60% of the total dry weight, exclusive of the weight of other intentionally included compounds. Preferably, for such preparations containing two or more proteins of the invention, the total weight of the proteins of the invention should be at least 75%, more preferably at least 90%, and most preferably at least 99%, of the total dry weight of the preparation, exclusive of the weight of other intentionally included compounds. Thus, if the proteins of the invention are mixed with one or more other compounds (e.g., diluents, detergents, excipients, salts, sugars, lipids) for purposes of administration, stability, storage, and the like, the weight of such other compounds is ignored in the calculation of the purity of the preparation.

As used herein, the term "contacted" as in the phrase "A is contacted with B," means that A and B are brought into sufficient physical proximity to interact at the molecular level, as by mixing A and B together in a solution, or pouring a solution of A over B on substrate. As used herein, the phrase "A is contacted with B" is intended to be equivalent to "B is contacted with A" and is not intended to imply that either element is fixed relative to the other, or that either element is moved relative to the other.

As used herein, the terms "modulate" or "affect" mean to either increase or decrease. As used herein, the terms "increase" and "decrease" mean, respectively, statistically significantly increase (i.e., $p<0.1$) and statistically significantly decrease (i.e., $p<0.1$).

General Considerations.

The present invention depends, in part, upon the identification, isolation and characterization of a cation channel protein which is expressed in sperm cells, but not in other tissues tested, and which plays a significant role in the motility of sperm and their ability to fertilize ova. The protein has been designated CatSper1 to indicate that it is the first Cation channel which is Sperm-specific to be identified. Significantly, inhibition of the activity of CatSper1 causes a substantial decrease in the motility of sperm cells, particularly the most vigorous sperm tail beating required for penetration of the zona pellucida (ZP) and subsequent fertilization. Therefore, inhibitors of the activity of the CatSper1 protein can prevent penetration of the ZP and can be used as male contraceptives in men or women to cause temporary, reversible infertility.

The CatSper1 amino acid sequence most closely resembles a single 6 transmembrane spanning repeat of the voltage-dependent $Ca^{2+}$ channel ($Ca_V$) four repeat structure. As detailed in the examples below, CatSper1 is located specifically in the principal piece of the sperm tail, and targeted disruption of the gene results in male sterility in otherwise normal mice. Sperm motility of the CatSper1$^{-/-}$ mice was dramatically decreased and they were unable to fertilize intact ova. In addition, cAMP-induced $Ca^{2+}$ influx was abolished in the sperm of mutant mice. CatSper1 is thus crucial to cAMP-mediated $Ca^{2+}$ influx, sperm motility, and fertilization. Therefore, CatSper1 represents an excellent target for non-hormonal contraceptives for both males and females, including humans and other mammals. Identification of the CatSper1 gene and protein also presents new targets for the diagnosis and treatment of infertility, and thus provides for new assays for the identification of compounds that can modulate fertility.

CatSper1 Nucleic Acids.

In one aspect, the present invention provides nucleic acid molecules, or nucleic acid analogs, encoding the CatSper1 proteins, or useful fragments thereof. The full length cDNA of the human CatSper1 gene is disclosed as SEQ ID NO: 1 and as GenBank Accession No. AF407333. The full-length cDNA sequence of a murine homolog is disclosed as SEQ ID NO: 3 and as GenBank Accession No. AF407332. A 5' regulatory region of the murine homolog, including 926 bases extending 5' from the translational start codon, is disclosed as SEQ ID NO: 5. A 3' regulatory region of the murine homolog, including 498 bases extending 3' from the translational termination codon, is disclosed as SEQ ID NO: 6.

Nucleic acid molecules of the invention may be DNA or RNA molecules, or hybrid DNA-RNA molecules. The nucleic acid analogs of the invention may be any of those known in the art, such as peptide nucleic acids, analogs including modified bases (e.g., 2'-halogeno-2'-dexynucleosides) and/or analogs including modified internucleoside linkages (e.g., phosphorothioate linkages), which are useful in applications such as in vitro translation or antisense technologies. In the remainder of this disclosure and the appended claims, whenever the term "nucleic acids" is used, the term is intended to embrace nucleic acid analogs when such analogs would be useful or suitable in the context of the usage. The nucleic acids may be sense molecules corresponding to all or a portion of a CatSper1 gene sequence, or may be antisense molecules which are complementary to all or a portion of a CatSper1 gene sequence. The nucleic acids may be derived from or correspond to genomic DNA or cDNA, or may be synthetic molecules based upon a CatSper1 protein sequence and the genetic code (e.g., synthetic nucleic acids which reflect the codon usage preferences in the host cells used in an expression systems).

In some embodiments, the CatSper1 nucleic acids comprise the entire coding region of a CatSper1 gene (e.g., SEQ ID NO: 1 or SEQ ID NO: 3). Such nucleic acids can be used to produce genetic constructs for transformation of cells, or for in vitro transcription and translation systems. Such nucleic acids can also be used as probes in hybridization assays to detect CatSper1 sequences in samples of other nucleic acids.

In other embodiments, subsets of the CatSper1 nucleic acid sequences are provided for use as primers for nucleic acid amplification reactions, as probes in hybridization assays to detect CatSper1 sequences in samples of other nucleic acids, or as probes to distinguish normal or wild-type sequence from abnormal or mutant sequences. In these embodiments, the nucleic acids of the invention comprise at 10, preferably at least 12, more preferably at least 14 and most preferably at least 16 consecutive nucleotides selected from a CatSper1 sequence such as SEQ ID NO: 1. Depending upon the nature of the application, it may be preferable to choose CatSper1 sequences which will have unique targets, or which are expected to have unique targets, within a sample being probed or amplified. Thus, for example, sequences which are longer and sequences which do not include frequently repeated elements (for example, polyadenylation signals) are more likely to be uniquely represented within any given sample. For purposes of choosing primers for amplification reactions, sequences of at least 15, and preferably 18-25 nucleotides are preferred.

In certain preferred embodiments, nucleic acids are provided which encode structural domains of a CatSper1 protein, or which encode fragments of the protein which may serve as epitopes for the generation of antibodies. Thus, for example, preferred nucleic acids include those encoding the transmembrane domains of the CatSper1 proteins (i.e., approximately residues 447-468, 481-502, 516-533, 542-563, 583-604 and 649-670 of SEQ ID NO: 2, approximately residues 351-372, 385-406, 419-438, 448-469, 489-510, and 555-576 of SEQ ID NO: 4, and allelic variants and homologs thereof), encoding the extracellular loops between transmembrane domains (i.e., approximately residues 469-480, 534-541, and 605-648 of SEQ ID NO: 2, approximately residues 373-384, 439-448, and 511-554 of SEQ ID NO: 4, and allelic variants and homologs thereof), or encoding the pore region (i.e., approximately residues 616-635 of SEQ ID NO: 2, approximately residues 522-541 of SEQ ID NO: 4, and allelic variants and homologs thereof). Other preferred nucleic acids include those encoding epitopes of the CatSper1 proteins having high predicted antigenicity, as identified by standard sequence analysis techniques described below. Thus, for example, preferred nucleic acids include those encoding sequences within approximately residues 2-34, 52-70, 108-130, 264-305, 387-417, and 606-614 of SEQ ID NO: 2, approximately residues 2-40, 120-148, 160-200, and 512-520 of SEQ ID NO: 4, and allelic and mammalian homologs thereof.

In certain embodiments, nucleic acids are provided which encode polypeptides have at least 80%, and preferably at least 85%, 90% or 95% amino acid sequence identity with at least a structural domain of a CatSper1 protein. Thus, in some embodiments, a nucleic acid is provided which encodes a polypeptide having at least 80%, 85%, 90% or 95% amino acid sequence identity with a transmembrane domain of a CatSper1 proteins (e.g., approximately residues 447-468, 481-502, 516-533, 542-563, 583-604 and 649-670 of SEQ ID NO: 2, approximately residues 351-372, 385-406, 419-438, 448-469, 489-510, and 555-576 of SEQ ID NO: 4, and allelic variants and homologs thereof), an extracellular loop between transmembrane domains (e.g., approximately residues 469-480, 534-541, and 605-648 of SEQ ID NO: 2, approximately residues 373-384, 439-448, and 511-554 of SEQ ID NO: 4, and allelic variants and homologs thereof), or a pore region (e.g., approximately residues 616-635 of SEQ ID NO: 2, approximately residues 522-541 of SEQ ID NO: 4, and allelic variants and homologs thereof). In some preferred embodiments, nucleic acids are provided encoding a polypeptide having at least 80%, 85%, 90% or 95% amino acid sequence identity with a CatSper1 protein and having CatSper1 activity. The ability of a protein to exhibit CatSper1 activity can be measured by its ability to complement a CatSper1 –/– mutant (e.g., a CatSper1 knock-out mutant) and restore a normal or CatSper1 +/+ phenotype (e.g., to restore sperm motility) in a cell otherwise capable of expressing CatSper1 activity (e.g., a sperm cell from the CatSper1 −/− mutant).

In other embodiments, isolated nucleic acids are provided which include a nucleotide sequence that hybridizes to at least a portion of a CatSper1 coding sequence (e.g., SEQ ID NO: 1 or SEQ ID NO: 3) under stringent hybridization conditions. Such conditions include hybridizations employing a wash step of 1.0×SSC at 65° C., and equivalents thereof. More stringent conditions can include wash steps of 0.5×SSC, 0.2× SSC, or even 0.1×SSC. Other equivalently stringent conditions are well known in the art. See, e.g., Ausubel et al., eds. (1989), Current Protocols in Molecular Biology, Vol. I, John Wiley & Sons, Inc., New York. In preferred embodiments, the nucleic acid encodes a polypeptide having CatSper1 activity.

In another aspect, the invention provides nucleic acids, either isolated or existing within cells, in which a nucleotide sequence encoding a polypeptide having CatSper1 activity is operably joined to a heterologous regulatory region such that the CatSper1 sequence is expressed. Thus, in certain embodiments, a heterologous regulatory region may be inserted into a chromosome such that it is operably joined to an endogenous CatSper1 sequence. In some embodiments, the polypeptide has at least 80%, 85%, 90% or 95% amino acid sequence identity with an amino acid sequence of SEQ ID NO: 2 or 4. In other embodiments, the nucleic acid encoding the polypeptide hybridizes to at least a portion of a nucleic acid of SEQ ID NO: 1 or SEQ ID NO: 3 under conditions including a wash step of 1.0×SSC at 65° C., 0.5×SSC, 0.2× SSC, or 0.1×SSC.

In certain embodiments, the nucleic acids of the invention encode polypeptides including a CatSper1 sequence of at least 50 amino acid residues in length, and preferably at least 100, 200 or 300 amino acid residues in length. These polypeptides can include a CatSper1 sequence which includes at least one transmembrane domain, at least one extracellular loop domain, at least a pore region, or combinations thereof. In some preferred embodiments, the polypeptide has CatSper1 activity. Such activity may include induction of ion current; mediation of cAMP-induced $Ca^{2+}$ influx; restoration of sperm motility when expressed in CatSper1 −/− sperm; and/or restoration of the ability to penetrate eggs when expressed in CatSper1 −/− sperm.

In another aspect, the invention provides kits for detecting at least a portion of a CatSper1 nucleic acid (i.e., CatSper1 genomic DNA, mRNA, cDNA or amplification products thereof). The kits include an isolated nucleic acid of the invention as a probe and means for detecting the probe. The means for detecting the probe can be a detectable label bound to the probe or a secondary nucleic acid probe for detecting the first probe (e.g., labeled secondary nucleic acid which specifically hybridizes to the isolated nucleic acid.).

Genetic Constructs.

In another aspect, the present invention provides genetic constructs comprising sequences selected from CatSper1 genes. In certain embodiments, the CatSper1 gene sequences are selected from the coding region of the CatSper1 gene, and in other embodiments, the CatSper1 gene sequences can be chosen from the CatSper1 regulatory regions extending approximately 500-1,500 bases, or approximately 600-1,000 bases, 5' of the start codon, and approximately 250-1,000 bases, or approximately 500-750 bases, 3' of the termination codon.

In one series of embodiments, CatSper1 coding sequences (e.g., the entire coding region, sequences encoding structural domains, sequences encoding potential epitopes, or sequences encoding useful primers or probes) are operably joined to an endogenous or exogenous regulatory region to form an expression construct. Useful regulatory regions for these purposes include the endogenous CatSper1 regulatory region, constitutive promoter sequences (e.g., CMV, SV40, EF2), inducible promoter sequences (e.g., lacZ, tet). Many useful vector systems are now widely available. For example, useful bacterial vectors include, but are not limited to, PQE70, pQE60, pQE-9 (Qiagen, Valencia, Calif.), pBluescript II (Stratagene, La Jolla, Calif.), and pTRC99a, pKK223-3, pDR540 and pRIT2T (Pharmacia, Piscataway, N.J.), pTrc (Amann et al. (1988), Gene 69:301-315) and pET 11d (Studier et al. (1990), Methods in Enzymol. 185:60-89). Examples of vectors for expression in yeast include pYepSec1 (Baldari et al. (1987), EMBO J. 6:229-234), pMFa (Kurjan et al. (1982), Cell 30:933-943), pJRY88 (Schultz et al. (1987), Gene 54:113-123), and pYES2 (Invitrogen Corporation, San Diego, Calif.). The CatSper1 proteins can also be expressed in insect cells (e.g., Sf 9 cells) using, for example, baculovirus expression vectors including, but not limited to, pAc vectors (Smith et al. (1983), Mol. Cell Biol. 3:2156-2165) and pVL vectors (Lucklow et al. (1989), Virology 170:31-39). Examples of mammalian expression vectors include, but are not limited to, pCDM8 (Seed (1987), Nature 329:840) and pMT2PC (Kaufman et al. (1987), EMBO J. 6:187-195). Other useful eukaryotic vectors include, but are not limited to, pXT1, pSG5 (Stratagene, La Jolla, Calif.), and pSVK3, pBPV, pMSG, and PSVLSV40 (Pharmacia, Piscataway, N.J.). Thus, one of ordinary skill in the art can choose a vector system appropriate to the host cell to be transformed.

In other embodiments, the vectors comprise defective or partial CatSper1 sequences in a "knock-out" vector. Such vectors are well-known in the art and can be used to produce a transgenic organism in which an endogenous gene is "knocked-out" by recombination with a partially homologous exogenous sequence which introduces a mutation within the endogenous sequence. Typically, the vector is directed at an endogenous target sequences which may be all or part of a gene of interest. The vector includes 5' and 3' flanking sequences which are homologous to the 5' and 3' ends of the target. Between the 5' and 3' flanking sequences is the sequence including the mutation. The mutation can be a termination mutation, frame-shift mutation, large deletion, or even the introduction of a new coding sequence which serves both to disrupt the endogenous gene and to act as a marker for successful homologous recombination. Knock-out vectors are further discussed below.

In other embodiments, the CatSper1 coding sequences can be joined to regulatory regions and heterologous coding sequences to form a genetic construct or fusion vector which encodes a fusion protein. Fusion vectors and fusion proteins can be useful to increase the expression of the CatSper1 protein, to increase the solubility of the CatSper1 protein, and aid in the purification of the CatSper1 protein (e.g., by acting as a ligand for affinity purification). A proteolytic cleavage site may be introduced at the junction of the CatSper1 and non-CatSper1 protein sequences so that the CatSper1 protein can easily be separated from the fusion moiety. Typical fusion expression vectors include pGEX (Smith et al. (1988), Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

In another series of embodiments, vectors or genetic constructs are produced in which the coding region from a reporter gene is operably joined to the regulatory region of a CatSper1 gene (e.g., SEQ ID NO: 5 at the 5' end and, optionally, SEQ ID NO: 6 at the 3' end). Such genetic constructs are useful in assays to identify or characterize compounds that enhance or repress CatSper1 gene expression by enhancing or repressing transcription of the CatSper1 gene. A wide variety of suitable reporter genes are known to those of skill in the art, and are commercially available. Examples include, but are not limited to, the lacZ and luciferase genes.

Useful CatSper1 regulatory elements include sequences having at least 80% nucleotide identity to at least 100 consecutive nucleotides selected from SEQ ID NO: 5, preferably at least 200 consecutive nucleotides, and more preferably at least 300-500 consecutive nucleotides. Useful regulatory elements will retain the ability to promote transcription of a coding sequence operably joined to the element in a mammalian cell in which a CatSper1 gene is expressed. In particular, useful regulatory elements will retain the ability to promote transcription in cells in which the CatSper1 gene from which the element was derived is expressed, or in which a homolog of that CatSper1 gene is expressed.

Transformed Cell Lines.

In another aspect, the present invention provides cell lines transformed with the nucleic acid molecules of the invention. Such cell lines can simply propagate these nucleic acids (e.g., when transformed with cloning vectors) or can express the polypeptides encoded by these nucleic acids (e.g., when transformed with expression vectors). Such transformed cell lines may be used to produce the CatSper1 proteins and CatSper1 fragments of the invention, or may be used in assays to screen for compounds that enhance, repress, agonize, or antagonize CatSper1 expression or activity.

The transformed cells may be produced by introducing into a cell an exogenous nucleic acid or nucleic acid analog which replicates within that cell, that encodes a polypeptide sequence which is expressed in that cell, and/or that is integrated into the genome of that cell so as to affect the expression of a genetic locus. The transformation may be achieved by any of the standard methods referred to in the art as transformation, transfection, transduction, electroporation, ballistic injection, and the like. The method of transformation is chosen to be suitable to the type of cells being transformed and the nature of the genetic construct being introduced into the cells.

Preferred cell lines for transformation include bacterial cells (e.g., *Escherichia coli*), yeast cells (e.g., *Saccharomyces cerevisiae*), insect cells (e.g., *Drosophila melanogaster* Schneider cells), nematode cells (e.g., *Caenorhabditis elegans*), amphibian cells (e.g., *Xenopus oocytes*), rodent cells (e.g., *Mus musculus* (e.g., murine 3T3 fibroblasts), *Rattus rattus*, Chinese Hamster Ovary cells (e.g., CHO-K1)), and human cells (e.g., human skin fibroblasts, human embryonic kidney cells (e.g., HEK-293 cells), COS cells). Transformed mammalian cells useful in the invention include somatic cells, fetal cells, embryonic stem cells, zygotes, gametes, germ line cells and transgenic animal cells. Although these and many other types of cells may be transformed for purposes of producing the CatSper1 protein, preliminary studies have found that transformation of *Xenopus* oocytes, CHO-K1 and HEK-293 cells does not result in detectable CatSper1 activity as determined by patch-clamp measurements of channel currents. These latter cells appear to lack co-factors or accessory proteins present in the principal piece of sperm that are necessary to CatSper1 activity, structural attributes of the principal piece which are necessary for functional channel organization, or a necessary CatSper1 post-translational processing or localization mechanism. Yeast two hybrid approaches and co-immunoprecipitation approaches can be used to screen libraries to identify CatSper1 accessory, associating or interacting proteins, including modulators of CatSper1 activity.

Appropriate cells may be transformed with any of the above-described genetic constructs in order to produce CatSper1 proteins, including fragments of CatSper1 proteins, fusion proteins of CatSper1 proteins, or marker proteins under the control of a CatSper1 regulatory region.

The cells may be transformed according to any method known in the art appropriate to the cell type being transformed. Appropriate methods can include those described generally in, e.g., Sambrook et al. (1989), *Molecular Cloning: A Laboratory Manual*, Cold Spring Harbor Laboratories, New York; and Davis et al. (1986), *Basic Methods in Molecular Biology*, Elsevier. Particular methods include calcium phosphate co-precipitation (Graham et al. (1973), *Virol.* 52:456-467), direct micro-injection into cultured cells (Capecchi (1980), *Cell* 22:479-488), electroporation (Shigekawa et al. (1988), *BioTechniques* 6:742-751), liposome-mediated gene transfer (Mannino et al. (1988), *BioTechniques* 6:682-690), lipid-mediated transduction (Felgner et al. (1987), *Proc. Natl. Acad. Sci. USA* 84:7413-7417), and nucleic acid delivery using high-velocity microprojectiles (Klein et al. (1987), *Nature* 327:70-73).

Transgenic Animals.

The present invention also provides for the production of transgenic non-human animal models in which wild type, allelic variant, chimeric, or antisense CatSper1 sequences are expressed, or in which CatSper1 sequences have been inactivated or deleted (e.g., "knock-out" constructs) or replaced with reporter or marker genes (e.g., "knock-in reporter" constructs). The CatSper1 sequences may be conspecific to the transgenic animal (e.g., murine sequences in a transgenic mouse) or transpacific to the transgenic animal (e.g. human sequence in a transgenic mouse). In such a transgenic animal, the transgenic sequences may be expressed inducibly, constitutively or ectopically. Expression may be tissue-specific or organism-wide. Engineered expression of CatSper1 sequences in tissues and cells not normally containing CatSper1 gene products may cause novel alterations of cation flux and lead to novel cell or tissue phenotypes. Ectopic or altered levels of expression of CatSper1 sequences may alter cell, tissue and/or developmental phenotypes. Transgenic animals are useful as models of disorders arising from defects in CatSper1 activity.

Transgenic animals are also useful for screening compounds for their effects on CatSper1 activity. Transgenic animals transformed with reporter constructs may be used to measure the transcriptional effects of small molecules or drugs or physical perturbations on the expression of CatSper1 genes and proteins in vivo. The transgenic animals of the invention, may be used to screen such compounds for therapeutic utility.

Animal species suitable for use in the animal models of the present invention include, but are not limited to, rats, mice, hamsters, guinea pigs, rabbits, dogs, cats, goats, sheep, pigs, and non-human primates (e.g., Rhesus monkeys, chimpanzees). For initial studies, transgenic rodents (e.g., mice) are preferred due to their relative ease of maintenance and shorter life spans. Transgenic non-human primates may be preferred for longer term studies due to their greater similarity to humans.

Using the nucleic acids disclosed and otherwise enabled herein, there are several available approaches for the creation of a transgenic animal. Thus, the enabled animal models include: (1) animals in which sequences encoding at least a functional fragment of a CatSper1 gene has been recombinantly introduced into the genome of the animal as an additional gene, under the regulation of either an exogenous or an endogenous promoter element, and as either a minigene (i.e., a genetic construct of the CatSper1 gene based on cDNA with introns removed) or a large genomic fragment; (2) animals in which sequences encoding at least a functional fragment of a CatSper1 gene have been recombinantly substituted for one or both copies of the animal's endogenous CatSper1 gene by homologous recombination or gene targeting; (3) animals in which one or both copies of one of the animal's homologous CatSper1 genes have been recombinantly "humanized" by the partial substitution of sequences encoding the human homolog by homologous recombination or gene targeting; (4) animals in which sequences encoding a reporter gene have replaced the endogenous CatSper1 gene by homologous recombination; (5) and "knock-out" animals in which one or both copies of the animal's CatSper1 sequences have been partially or completely inactivated by the insertion, deletion or substitution of one or more nucleotides by homologous recombination. These and other transgenic animals of the invention are useful as models of infertility or other disorders arising from defects in the CatSper1 gene and/or protein. These animals are also useful for screening compounds for their effects on the CatSper1 gene and/or protein.

To produce an animal model (e.g., a transgenic mouse), a wild type or allelic variant CatSper1 sequence or a wild type or allelic variant of a recombinant nucleic acid encoding at least a functional fragment of a CatSper1 protein is preferably inserted into a germ line or stem cell using standard techniques of oocyte or embryonic stem cell microinjection, or other form of transformation of such cells. Alternatively, other cells from an adult organism may be employed. Animals produced by these or similar processes are referred to as transgenic. Similarly, if it is desired to inactivate or replace an endogenous CatSper1 sequence, homologous recombination using oocytes, embryonic stem or other cells may be employed. Animals produced by these or similar processes are referred to as "knock-out" (inactivation) or "knock-in" (replacement) models.

For oocyte injection, one or more copies of the recombinant DNA constructs of the present invention may be inserted into the pronucleus of a just-fertilized oocyte. This oocyte is then reimplanted into a pseudo-pregnant foster mother. The live born animals are screened for integrants using standard DNA/mRNA analysis (e.g., from the tail veins of offspring mice) for the presence of the inserted recombinant transgene sequences. The transgene may be either a complete genomic sequence introduced into a host as part of a yeast artificial chromosome (YAC), bacterial artificial chromosome (BAC), or other chromosome DNA fragment; as a cDNA with either the endogenous promoter or a heterologous promoter; or as a minigene containing all of the coding regions and other elements found to be necessary for optimum expression.

To create a transgene, the target sequence of interest (e.g., a wild type or allelic variant of a CatSper1 sequence) is typically ligated into a cloning site located downstream of a promoter element which will regulate the expression of RNA from the sequence. Downstream of the coding sequence, there is typically a polyadenylation sequence. An alternative approach to creating a transgene is to use an exogenous promoter and regulatory sequences to drive expression of the transgene. Finally, it is possible to create transgenes using large genomic DNA fragments such as YACs which contain the entire desired gene as well as its appropriate regulatory sequences.

Animal models may be created by targeting endogenous CatSper1 sequences for homologous recombination. These targeting events can have the effect of removing endogenous sequence (knock-out) or altering the endogenous sequence to create an amino acid change associated with human disease or an otherwise abnormal sequence (e.g., a sequence which is more like the human sequence than the original animal sequence) (knock-in animal models). A large number of vectors are available to accomplish this and appropriate sources of genomic DNA for mouse and other animal genomes to be targeted are commercially available (e.g., GenomeSystems Inc., St. Louis, Mo.).

The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of the sequences included in the vector. Alternatively, the sequences can be chosen to cause deletion of sequences that would normally reside between the left and right arms of the vector surrounding the neomycin cassette. The former is known as a knock-in, the latter is known as a knock-out.

Retroviral infection of early embryos can also be done to insert the recombinant DNA constructs of the invention. In this method, the transgene (e.g., a wild type or allelic variant of a CatSper1 sequence) is inserted into a retroviral vector which is used to directly infect embryos (e.g., mouse or non-human primate embryos) during the early stages of development to generate partially transgenic animals, some of which bear the transgenes in germ line cells.

Alternatively, homologous recombination using a population of stem cells allows for the screening of the population for successful transformants. Once identified, these can be injected into blastocysts, and a proportion of the resulting animals will show germ line transmission of the transgene.

Techniques of generating transgenic animals, as well as techniques for homologous recombination or gene targeting, are now widely accepted and practiced. A laboratory manual on the manipulation of the mouse embryo, for example, is available which details standard laboratory techniques for the production of transgenic mice (Hogan, et al. (1986), Manipulating the Mouse Embryo, Cold Spring Harbor Laboratory Press, Cold Spring Harbor, N.Y.).

Details of the actual production of CatSper1 knock-out mice are provided in Example 3 below.

CatSper1 Proteins and Polypeptides.

In another aspect, the present invention provides substantially pure preparations of CatSper1 proteins. The proteins can be isolated from sperm cells, using standard techniques such as immunoaffinity purification with the antibodies of the invention (see below), but are preferably isolated from the transformed cells of the invention, in which they may be expressed at higher levels and, optionally, as fusion proteins which are more easily isolated and/or purified.

In some embodiments, the CatSper1 proteins comprise the entire translated sequence of the CatSper1 coding region. Examples of such full-length CatSper1 proteins include the human CatSper1 protein disclosed as SEQ ID NO: 2 and the mouse homolog disclosed as SEQ ID NO: 4, as well as other CatSper1 proteins, including allelic and mammalian homologs of these human CatSper1 proteins, and functional equivalents thereof.

In other embodiments, the CatSper1 proteins are CatSper1 fragments. Such fragments include the structural domains of the CatSper1 proteins, including the transmembrane, loop and pore-forming regions of the proteins. Preferred structural domains include the transmembrane domains of the human CatSper1 protein (i.e., approximately residues 447-468, 481-502, 516-533, 542-563, 583-604 and 649-670 of SEQ ID NO: 2, approximately residues 351-372, 385-406, 419-438, 448-469, 489-510, and 555-576 of SEQ ID NO: 4, the extracellular loops between transmembrane domains (i.e., approximately residues 469-480, 534-541, and 605-648 of SEQ ID NO: 2, approximately residues 373-384, 439-448, and 511-554 of SEQ ID NO: 4), and the pore region (i.e., approximately residues 616-635 of SEQ ID NO: 2, approximately residues 522-541 of SEQ ID NO: 4), as well as allelic variants and homologs thereof. Other CatSper1 fragments include potentially useful epitopes of the CatSper1 proteins, as identified by standard sequence analysis techniques described below. Thus, for example, preferred CatSper1 fragments include human CatSper1 sequences within approximately residues 2-34, 52-70, 108-130, 264-305, 387-417, and 606-614 of SEQ ID NO: 2, approximately residues 2-40, 120-148, 160-200, and 512-520 of SEQ ID NO: 4, and allelic and mammalian homologs thereof.

In certain embodiments, polypeptides are provided having at least 80%, and preferably at least 85%, 90% or 95% amino acid sequence identity with at least a structural domain of a CatSper1 protein. Thus, in some embodiments, a polypeptide is provided having at least 80%, 85%, 90% or 95% amino acid sequence identity with a transmembrane domain of a CatSper1 proteins (e.g., approximately residues 447-468, 481-502, 516-533, 542-563, 583-604 and 649-670 of SEQ ID NO: 2, approximately residues 351-372, 385-406, 419-438, 448-469, 489-510, and 555-576 of SEQ ID NO: 4, and allelic variants and homologs thereof), an extracellular loop between transmembrane domains (e.g., approximately residues 469480, 534-541, and 605-648 of SEQ ID NO: 2, approximately residues 373-384, 439-448, and 511-554 of SEQ ID NO: 4, and allelic variants and homologs thereof), or a pore region (e.g., approximately residues 616-635 of SEQ ID NO: 2, approximately residues 522-541 of SEQ ID NO: 4, and allelic variants and homologs thereof). In some preferred embodiments, polypeptides are provided having at least 80%, 85%, 90% or 95% amino acid sequence identity with a CatSper1 protein and having CatSper1 activity. The ability of a protein to exhibit CatSper1 activity can be measured by its ability to complement a CatSper1 −/− mutant (e.g., a CatSper1 knock-out mutant) and restore a normal or CatSper1 +/+ phenotype (e.g., to restore sperm motility) in a cell otherwise capable of expressing CatSper1 activity (e.g., a sperm cell from the CatSper1 −/− mutant).

In certain embodiments, the polypeptides of the invention include a CatSper1 sequence of at least 50 amino acid residues in length, and preferably at least 100, 200 or 300 amino acid residues in length. These polypeptides can include a CatSper1 sequence which includes at least one transmembrane domain, at least one extracellular loop domain, at least a pore region, or combinations thereof. In some preferred embodiments, the polypeptide has CatSper1 activity. Such activity may include induction of ion current when expressed in a cell (e.g., an oocyte); mediation of cAMP-induced Ca influx; restoration of sperm motility when expressed in CatSper1 −/− sperm; and/or restoration of the ability to penetrate eggs when expressed in CatSper1 −/− sperm.

Antibodies Against CatSper1 Proteins and Polypeptides.

In another aspect, the present invention provides substantially pure preparations of antibodies against the CatSper1 proteins, and methods of making such antibodies. In particular, the invention provides antibodies raised against CatSper1 epitopes having high predicted antigenicity, which therefore will selectively bind to and, thereby, isolate or identify wild type and/or variant forms of the CatSper1 proteins.

The antibodies may be raised against the full-length CatSper1 proteins, against fragments of the CatSper1 proteins, or using any CatSper1 epitope which is characteristic of the proteins and which substantially distinguishes them from other proteins. In preferred embodiments, the epitope is a protein sequence of at least 6-12, preferably 10-20, more preferably 15-30 consecutive amino acid residues of a CatSper1 protein. In particular embodiments, the antibodies are raised against CatSper1 epitopes selected from sequences within approximately residues 2-34, 52-70, 108-130, 264-305, 387-417, and 606-614 of SEQ ID NO: 2, and approximately residues 2-40, 120-148, 160-200, and 512-520 of SEQ ID NO: 4. Other preferred epitopes include allelic and mammalian homologs of these epitopes. Epitopes having a high predicted antigenicity were identified by prediction of hydrophobicity, surface probability and antigenic index using standard programs, including GCG and MacVector (Genetics Computer Group, University of Wisconsin Biotechnology Center, Madison, Wis.; Accelrys Inc., San Diego, Calif.). See also, Jameson and Wolf (1988), Comput. Appl. Biosci. 4:181-186.

CatSper1 immunogen preparations may be produced from crude extracts (e.g., microsomal fractions of cells expressing the proteins), from proteins or peptides substantially purified from cells which naturally or recombinantly express them or, for small immunogens, by chemical peptide synthesis. The CatSper1 immunogens may also be in the form of a fusion protein in which the non CatSper1 region is chosen for its adjuvant properties and/or the ability to facilitate purification.

The antibodies of the invention may be polyclonal or monoclonal, or may be antibody fragments, including Fab fragments, $F(ab')_2$ fragments, Fv fragments, and single chain Fv fragments (scFv). In addition, after identifying useful antibodies by the method of the invention, recombinant antibodies may be generated, including any of the antibody fragments listed above, as well as chimeric and/or humanized antibodies based upon non-human antibodies to the CatSper1 proteins. In light of the present disclosure of CatSper1 proteins, as well as the characterization of other CatSper1 proteins enabled herein, one of ordinary skill in the art may produce the above-described antibodies by any of a variety of standard means. For an overview of antibody techniques, see Antibody Engineering, 2nd Ed., Borrebaek, ed., Oxford University Press, Oxford (1995).

As a general matter, monoclonal anti-CatSper1 antibodies can be produced by first injecting a mouse, rabbit, goat or other suitable animal with a CatSper1 immunogen in a suitable carrier or diluent. Carrier proteins or adjuvants can be utilized, and booster injections (e.g., bi- or tri-weekly over 8-10 weeks) can be employed as necessary. After allowing for development of a humoral response, the animals are sacrificed and their spleens are removed and resuspended in an appropriate buffer (e.g., phosphate buffered saline). The spleen cells serve as a source of lymphocytes, some of which will produce antibodies of the appropriate specificity. These cells are then fused with an immortalized cell line (e.g., a myeloma), and the products of the fusion are plated into tissue culture wells in the presence of a selective agent (e.g., HAT). The wells are serially screened and replated, selecting cells making a useful antibody each time. Typically, several screening and replating procedures are carried out until the wells contain single clones which are positive for antibody production. Monoclonal antibodies produced by such clones may be purified by standard methods such as affinity chromatography using Protein A Sepharose, by ion-exchange chromatography, or by variations and combinations of these techniques.

Antibodies of the invention may be used in a variety of applications. For example, antibodies may be used in a purification process (i.e., immunoaffinity purification) for CatSper1 proteins, in assays to detect the presence or level of CatSper1 protein in sperm (e.g., in a diagnostic test for a CatSper1-related disorder), or in assays to measure the presence or level of CatSper1 expression in transformed cells (e.g., in assays for regulators of CatSper1 expression, in Western blotting to identify cells expressing CatSper1 proteins, or in immunocytochemistry or immunofluorescence techniques to establish the cellular or extracellular location of CatSper1 proteins).

The antibodies of the invention may be bound or conjugated with other compounds or materials for diagnostic and/or therapeutic uses. For example, they may be coupled to labels such as radionuclides, fluorescent compounds (e.g., rhodamine), or enzymes for imaging or therapy. The labels maybe bound to the antibodies covalently or non-covalently.

In another aspect, the invention provides kits for detecting at least an epitope of a CatSper1 protein. The kits include an anti-CatSper1 antibody and a means for detecting the antibody. The means for detecting the antibody can be a detectable label bound to the antibody or secondary antibodies for detecting the anti-CatSper1 antibodies (e.g., a labeled goat anti-rabbit-Ig antibody as a secondary antibody for detecting a rabbit anti-CatSper1 antibody).

Assays for Modulators of CatSper1 Expression or Activity.

In another aspect, the present invention provides assays for modulators of CatSper1 expression or activity. The modulators may affect the transcription, translation, post-translational processing, localization, or activity of the CatSper1 gene and/or protein.

Thus, in one series of embodiments, the transformed cells of the invention are contacted with a candidate compound, and the effect of the compound on the expression or activity of CatSper1 is determined. As a general matter, the assays require contacting a candidate compound with a cell expressing a CatSper1 protein and measuring an indicator of CatSper1 activity in the cell. The indicator may be an indicator of transcription (e.g., mRNA levels), translation (e.g., protein levels), post-translational processing (e.g., specific glycosylation), localization (e.g., immunohistochemistry), or activity (e.g., sodium or other monovalent ion flux; calcium or other divalent ion flux). The indicator measurement is then compared to a reference level to determine whether the candidate compound caused an increase or decrease in the indicator. The reference level may be extrinsic (e.g., a predetermined baseline level) or intrinsic (e.g., a measurement of the same cell prior to contact with the candidate compound). If an increase or decrease is significant (based on a single reading or on multiple readings from one or more cells), the candidate compound is identified as a potential modulator of CatSper1 activity. Assays for changes in CatSper1 activity may include any of those used routinely in the art for other genes. For example, changes in the presence or levels of CatSper1 mRNA or protein may be detected to identify enhancers or repressors of CatSper1 expression. Alternatively, when using a reporter gene construct of the invention, the biochemical or phenotypic change characteristic of the reporter can be used as an indication that the candidate compound enhances or represses reporter gene expression. In other embodiments, changes in the activity of the CatSper1 protein can be detected by measuring, for example, the flux of cations mediated by the CatSper1 protein, or by measuring whole cell or channel currents. Measurements of ion fluxes can be facilitated by the use of chromophores which change color depending upon the concentration of specific ions. The effects of candidate compounds on mature sperm cells can be tested to confirm or validate results obtained in the transformed cells of the invention.

Compounds which bind to CatSper1 are candidates for modulating CatSper1 activity. Thus, in another series of embodiments, libraries of compounds may be screened to identify candidates for modulating CatSper1 activity by contacting candidate compounds with a CatSper1 protein, or at least a structural domain of a CatSper1 protein, to identify compounds that bind to CatSper1. CatSper1 structural domains which may be used in these methods include those described above (i.e., transmembrane domains, extracellular loops, pore regions), but extracellular loops and pore regions are preferred. In such methods, the CatSper1 protein or CatSper1 structural domain may be immobilized (e.g., on a column or microparticle) and a solution of the candidate compound may be contacted with the CatSper1 moiety, or the candidate compound may be immobilized (e.g., on a column or microparticle) and a solution of the CatSper1 moiety may be contacted with the candidate compound. Alternatively, in some embodiments, neither the candidate compound nor the CatSper1 moiety is immobilized but, rather, both are in solution and binding is detected by, for example, aggregation of particles bearing the binding partners. Binding may be detected by methods well known in the art (e.g., radioactive or fluorescent labeling of one component of the potential binding pair; plasmon-resonance detection of binding; turbidity changes in aggregation assays). Compounds which, under physiological conditions (e.g., within the testis or epididymis, or within the vagina, uterus or fallopian tubes), exhibit significant binding (e.g., $K_d \leq 10$ μM) to a CatSper1 protein, are potential modulators of CatSper1 activity.

Methods of Modulating Fertility.

The CatSper1 gene and protein are ideal targets for potential contraceptive drugs. Since in vitro fertilization results indicate that CatSper1$^{-/-}$ sperm are unable to fertilize ova, a specific blocker of CatSper1 might be effective when taken by either males or females. The restricted localization of CatSper1 to mature sperm means that a specific blocker should not affect other tissues and thus side effects should be low or nonexistent. Moreover, the normal development and behavior (including sexual) of the mutant mice supports such a prediction. Finally, since the channel represents a novel structure, it may be an excellent target for new channel agonists or antagonists.

Thus, in another aspect, the present invention provides methods of decreasing fertility by decreasing the expression or activity of a CatSper1 gene or protein. Such decreases in expression or activity can be achieved by means of a small molecule which represses expression of a CatSper1 gene, by means of an antisense molecule which inhibits the translation of a CatSper1 mRNA, by means of a small molecule that interferes with CatSper1 translation or post-translational processing, by means of a small molecule that interferes with CatSper1 localization, or by means of a molecule which blocks CatSper1 activity as an ion channel. Antibodies, including antibody fragments such as Fab fragments, F(ab')$_2$ fragments, Fv fragments, and single-chain Fv fragments (ScFv), also can be used to inhibit CatSper1 activity by binding to extracellular domains of the protein and thereby block its activity.

Because most repressors or antagonists of CatSper1 expression or activity will be reversible or will affect only mature sperm, the effects of such compounds on fertility will be reversible because the molecules will be cleared from the body over time and new sperm are constantly being produced. Thus, repressors or antagonists of CatSper1 expression or activity can be used as human contraceptives because they can cause reversible infertility. Such contraceptives can be taken orally or parenterally (e.g., injection, transdermal patch, or bioerodable implant) by females if they achieve sufficient concentrations in the vagina, uterus or fallopian tubes to effectively inhibit CatSper1 activity and thereby decrease sperm motility and the ability of sperm to penetrate the ZP. Similarly, such contraceptives can be taken orally or parenterally by males if they achieve sufficient concentration in the testes or seminal fluids to effectively inhibit CatSper1 expression or activity, and thereby decrease sperm motility and the ability of sperm to penetrate the ZP. Alternatively, such compounds can be formulated into lubricants, moisturizers, foams or jellies for use with prophylactics, cervical caps, or contraceptive vaginal sponges, foams or jellies.

In another series of embodiments, repressors or antagonists of CatSper1 genes and proteins can be used as contraceptives to treat non-human mammals. These embodiments are similar to those described above for human contraception. Such contraceptives can be used with respect to domesticated animals that are maintained as pets, with respect to other commercially valuable domesticated animals (e.g., cows, sheep, horses), or with respect to animal nuisances (e.g., mice, rats, raccoons, gophers). In some embodiments, the contraceptives are orally available and can be mixed into food sources for the animals. In other embodiments, the contraceptives can be administered parenterally (e.g., injection, transdermal patch, or bioerodable implant).

To the extent that the mammalian CatSper1 genes and proteins and the fish, amphibian and insect homologs of the CatSper1 genes and proteins share substantial sequence identity, repressors or antagonists of mammalian CatSper1 genes and proteins can also be used in the control of fish, amphibian and insect nuisances (e.g., mosquitoes). In addition, the non-mammalian homologs of the CatSper1 genes and proteins can be used to identify additional repressors and antagonists which are more specific or effective for such homologs.

Methods of CatSper1 Genotyping and Diagnosing CatSper1-Related Disorders.

In another aspect, the present invention provides methods for genotyping subjects with respect to the CatSper1 gene, and diagnosing CatSper1-related disorders such as infertility. Thus, for example, the CatSper1 nucleic acids (or a portion thereof) of a subject may be tested to ascertain whether that subject's CatSper1 genotype includes any mutations in the sequences relative to wild-type. Of particular significance would be mutations which introduce termination or frameshift mutations that prevent the production of functional CatSper1 proteins. Point mutations, however, can also be identified which cause decreased CatSper1 activity. Similarly, the antibodies of the present invention can be used to test the sperm of a subject to determine the presence or level of CatSper1 proteins. Of particular note would be an absence or significant decrease in the level of CatSper1 protein. Point mutations, however, can also cause infertility and can be detected by antibodies which are specific for epitopes including or affected by the mutant sequences. Determination of a subject's CatSper1 genotype can be used for genetic or reproductive counseling, or for diagnosing infertility that results from a CatSper1 defect.

To determine a subject's CatSper1 genotype, or for diagnosing a CatSper1-related disorder, the nucleic acids of the invention can be used as primers in polymerase chain reaction (PCR) (e.g., anchor PCR or RACE PCR), or ligase chain reaction (LCR) amplifications of the subject's DNA/mRNA. See, e.g., U.S. Pat. No. 4,683,195 and U.S. Pat. No. 4,683,202; Landegran et al. (1988), Science 241:1077-1080; Nakazawa et al. (1994), Proc. Natl. Acad. Sci. USA 91:360-364; and Abravaya et al. (1995), Nucleic Acids Res. 23:675-682. Other useful methods for amplifying a subjects DNA/mRNA using the nucleic acids of the invention include self-sustained sequence replication (e.g., Guatelli et al. (1990), Proc. Natl. Acad. Sci. USA 87:1874-1878), transcriptional amplification (e.g., Kwoh et al. (1989), Proc. Natl. Acad. Sci. USA 86:1173-1177), and Q-Beta Replicase-based systems (e.g., Lizardi et al. (1988), Bio/Technology 6:1197. The presence, absence or size of the resulting amplification products (e.g., Saiki et al. (1986), Nature 324:163; Saiki et al. (1989), Proc. Natl. Acad. Sci. USA 86:6230; Gibbs et al. (1989), Nucleic Acids Res. 17:2437-2448; Prossner (1993), Tibtech 11:238; Gasparini et al. (1992), Mol. Cell Probes 6:1; Barany (1991) Proc. Natl. Acad. Sci. USA 88:189), direct sequencing of the amplification products (e.g., Maxim and Gilbert (1977), Proc. Natl. Acad. Sci. USA 74:560; Sanger (1977), Proc. Natl. Acad. Sci. USA 74:5463), and other standard analytic techniques may be employed to determine CatSper1 genotypes. The amplified products can also be used in many of the techniques described below.

The nucleic acids of the invention also can be used as probes in hybridization and/or conformation-based assays to identify complementary or imperfectly complementary sequences in a subject.

For example, in some embodiments, mutations can be identified by selectively hybridizing sample nucleic acids to immobilized control nucleic acids. The controls can be adsorbed to filters or columns, or can be arranged in high density ordered arrays containing hundreds or thousands of oligonucleotides probes (see, e.g., Cronin et al. (1996), Human Mutation 7:244-255; Kozal et al. (1996), Nature Medicine 2:753-759).

In other embodiments, enzymatic or chemical cleavage may be employed to cleave or restrict duplexes of sample and control sequences at mismatched bases (e.g., Myers et al. (1985), *Science* 230:1242). For example, RNA/DNA duplexes can be treated with RNAse and DNA/DNA hybrids can be treated with S1 nuclease to digest duplexes at mismatched bases, G/A mismatches are cleaved at the A by the *E. coli* mutY enzyme, G/T mismatches are cleaved at the T by the human thymidine DNA glycosylase (see, e.g., Hsu et al. (1994), Carcinogenesis 15:1657-1662). Chemical cleavage of mismatches can be employed using, for example, hydroxylamine, osmium tetroxide and/or piperidine. See generally, e.g., Cotton et al. (1988), Proc. Natl. Acad. Sci. USA 85:4397; Saleeba et al. (1992), Methods Enzymol. 217:286-295; and U.S. Pat. No. 5,459,039.

In other embodiments, mutations can create or destroy specific sequences which serve cleavage points for restriction enzymes or ribozymes. Thus, restriction fragment length polymorphism (RFLP) analysis can be employed in which (amplified) sample DNA is digested with at least one restriction endonuclease, and the resulting fragment lengths are analyzed and compared to controls to determine the presence or absence of mutations which affect the pattern of restriction fragment lengths. Similarly, sequence-specific ribozymes can be used to identify mutations that create or destroy ribozyme cleavage sites. See, e.g., U.S. Pat. No. 5,498,531.

In other embodiments, mutations can be detected by their effect on the electrophoretic mobility of a sequence, either as a single-stranded nucleic acid or as duplex. For example, single-strand conformation polymorphism (SSCP) analysis (Orita et al. (1989), Proc. Natl. Acad. Sci. USA 86:2766; Cotton (1993), Mutat. Res. 285:125-144; Hayashi (1992), Genet. Anal. Tech. Appl. 9:73-79; and Keen et al. (1991), Trends Genet. 7:5). denaturing gradient gel electrophoresis (DGGE) (Myers et al. (1985), Nature 313:495). and temperature gradient gel electrophoresis (Rosenbaum and Reissner (1987), Biophys. Chem. 265:12753) can be employed.

These and other methods of detecting mutations in the CatSper1 genes and proteins will be apparent to one of ordinary skill in the art based upon the nucleic acid and protein sequences disclosed herein.

In Vitro Fertilization.

In another aspect, the present invention provides a method of in vitro fertilization of ova by sperm characterized by decreased CatSper1 expression or activity. As shown in the examples below, CatSper1-deficient sperm appear to be normal in all respects except in their motility and their ability to penetrate the ZP. Moreover, CatSper1-deficient sperm are capable of fertilizing ova from which the ZP has been removed. Thus, the present invention provides a method of in vitro fertilization for CatSper1-deficient males in which the sperms of such males are treated to overcome the CatSper1 deficiency or are contacted with ova from which the ZP have been removed. Because other genetic deficiencies may result in sperm which are incapable of penetrating the ZP, this method can be extended to other males having genetic deficiencies which affect ZP-penetration or for which in vitro fertilization previously has been unsuccessful using ova with intact ZPs.

Methods of Treating CatSper1-Mediated Infertility.

In another aspect, the present invention provides methods of treating infertility in CatSper1-deficient males, in which an enhancer of CatSper1 expression or an agonist of CatSper1 activity is administered to the subject. In other embodiments, gene or protein therapy may be employed to provide the CatSper1 gene or protein to sperm (or sperm progenitors) which are deficient in the CatSper1 gene or protein. For gene therapy, a genetic construct encoding a CatSper1 protein can be employed to cause expression of a CatSper1 protein in sperm or sperm progenitors which are deficient in the CatSper1 gene or protein.

In another aspect, infertility of a mating pair (e.g., a human couple) may result from antibodies generated by the female against antigens present on the sperm of the male. In some cases, the antibodies can be directed against an epitope of a CatSper1 protein. Thus, the present invention also provides methods of diagnosing an anti-CatSper1 antibody-mediated infertility caused by anti-CatSper1 antibodies present in a female urogenital tract. The methods include obtaining a sample of antibodies present in the female and contacting the antibodies with CatSper1 proteins or fragments of CatSper1 proteins. In some embodiments, the CatSper1 fragments are epitopes of the CatSper1 proteins having high predicted antigenicity (e.g., approximately residues 2-34, 52-70, 108-130, 264-305, 387-417, and 606-614 of SEQ ID NO: 2, approximately residues 2-40, 120-148, 160-200, and 512-520 of SEQ ID NO: 4, and allelic and mammalian homologs thereof). In these methods, either the female's antibodies or the CatSper1 proteins/fragments optionally can be immobilized and either the female's antibodies or the CatSper1 proteins/fragments optionally can be detectably labeled to facilitate detection of binding between the antibodies and the CatSper1 proteins/fragments.

In these cases, administering an excess of the CatSper1 protein, or at least a fragment of the CatSper1 protein including the relevant epitope, can saturate the binding sites of the anti-CatSper1 antibodies present in the female's urogenital tract and thereby inhibit or reduce the antibody-mediated infertility. Alternatively, an anti-idiotypic antibody (i.e., an antibody which specifically binds to the variable regions of another antibody with a defined specificity) can be employed. That is, an antibody which binds specifically to anti-CatSper1 antibodies can be employed to inhibit the anti-CatSper1 antibodies present in the female's urogenital tract and thereby inhibit or reduce the antibody-mediated infertility. One of ordinary skill in the art can easily identify the relevant CatSper1 epitopes recognized by such female antibodies (e.g., using the methods described above) and produce substantially pure preparations of the relevant epitope or anti-idiotypic antibodies by standard means. Thus, the invention also provides methods for treating an anti-CatSper1 antibody-mediated infertility caused by anti-CatSper1 antibodies present in a female urogenital tract. The methods include administering into the urogenital tract of the female an amount of the relevant CatSper1 epitope (or whole CatSper1 protein) or an amount an anti-idiotypic antibody effective to inhibit the anti-CatSper1 antibodies and thereby inhibit or reduce the antibody-mediated infertility.

Business Methods Relating to CatSper1.

In another aspect, the present invention provides a method of conducting a drug discovery business comprising: identifying, by the assays of the invention, one or more agents which antagonize CatSper1 activity; determining if an agent identified in such an assay, or an analog of such an agent, inhibits at least one of sperm motility or egg penetrance; conducting therapeutic profiling of an agent identified as an antagonist for efficacy and toxicity in one or more animal models; and formulating a pharmaceutical preparation including one or more antagonist agents identified as having an acceptable therapeutic profile.

In one embodiment, the drug discovery business further includes the step of establishing a system for distributing the pharmaceutical preparation for sale, and may optionally include establishing a sales group for marketing the pharmaceutical preparation.

In another aspect, the present invention provides a method of conducting a drug discovery business comprising: identifying, by the subject assay, one or more agents which agonize CatSper1 activity; determining if an agent identified in such an assay, or an analog of such an agent, increases at least one of sperm motility or egg penetrance; conducting therapeutic profiling of an agent identified as an agonist for efficacy and toxicity in one or more animal models; and formulating a pharmaceutical preparation including one or more agents identified as having an acceptable therapeutic profile.

In certain embodiments, the drug discovery business further includes the step of establishing a system for distributing the pharmaceutical preparation for sale, and may optionally include establishing a sales group for marketing the pharmaceutical preparation.

In certain embodiments, the assay to identify agents which agonize CatSper1 activity is conducted using wild type CatSper1. In another embodiment, the assay to identify agents which agonize CatSper1 activity is conducted using a mutant CatSper1. By a mutant CatSper1 is meant to include a CatSper1 polypeptide containing one or more insertions, deletions, or substitutions in amino acid sequence, wherein said insertions, deletions, or substitutions change the activity of the mutant CatSper1 in comparison to wild type CatSper1. Such a change in activity includes, but is not limited to, a change in motility, egg penetrance, cation transport. A change in activity would also include a change in the proper localization or expression of the CatSper1 protein or mRNA.

In still another aspect, the invention provides a method of conducting a reproductive medicine business comprising: examining a sperm sample from a male patient, wherein said patient is experiencing a fertility problem; determining if said sperm are characterized by at least one of a decrease in motility or a decrease in egg penetrance; performing in vitro analysis to determine the efficacy of a CatSper1 agonist in increasing at least one of sperm motility or egg penetrance; establishing a treatment regimen comprising administering an amount of a CatSper1 agonist effective to increase at least one of sperm motility or egg penetrance in said male.

In certain embodiments, the method further includes a step wherein said male patient is monitored by a physician to evaluate improvement in fertility. Such evaluation may include examination of sperm at regular intervals following the initiation of treatment to measure improvements in one or more of sperm motility or egg penetrance. The frequency of follow-up evaluation by the treating physician will be determined by the physician or a trained health care provider. Factors to consider are the patient's schedule and comfort level, as well as the urgency with which a male patient is attempting to father an offspring. Representative follow-up appointments may be conducted weekly, semi-weekly, or monthly. In another embodiment, the method further includes the step of billing the patient or the patient's insurance provider. We note that in cases where the patient's health insurance is paying for all or a portion of said fertility treatments, the policies of said health insurance provider will likely influence the frequency of follow-up appointments.

In yet another aspect, the present invention provides a method of conducting a contraceptive medicine business comprising: providing a pharmaceutical preparation discovered through the methods of a drug discovery business, wherein said preparation inhibits the activity of CatSper1; providing instructions to physicians and health care providers for the administration of an amount of said pharmaceutical preparation effective to inhibit the activity of CatSper1, wherein said effective amount is sufficient to prevent pregnancy.

In one embodiment, the method further includes the step of establishing a system for distributing the pharmaceutical preparation for sale, and may optionally include establishing a sales group for marketing the pharmaceutical preparation.

As described in further detail below, mice that are deficient in CatSper1 activity are infertile. The motility of the sperm from these mice, although normal in appearance, is significantly impaired. Additionally, said sperm are unable to effectively penetrate the zona pellucida of eggs. Accordingly, agents which antagonize the activity of CatSper1 have substantial utility as contraceptive agents.

CatSper1 encodes a cation channel. Numerous types of cation channels play critical roles in cellular processes including regulation of cardiac function (e.g., calcium channels). Thus, a great limitation of methods which employ administration of agents which either increase or decrease the activity of cation channels is that such methods are likely to have substantial side-effects. These side-effects may include significant cardiac complications. However, the results provided herein demonstrate that CatSper1 is specifically expressed in sperm. Accordingly, agents which increase or decrease the activity of CatSper1 can be administered to patients without the side effects associated with either general cation channel antagonists and agonists, or antagonists and agonists of cation channels which are more widely expressed in the body.

Through a drug discovery business, one or more agents which can antagonize the activity of CatSper1 can be identified. By antagonize the activity is meant to decrease, in whole or in part, the activity of CatSper1. Such a decrease in activity can be measured by examining at least one of sperm motility, egg penetrance, or cation transport. The terms decrease and antagonize will be used interchangeably throughout.

In certain embodiments, the initially identified CatSper1 agonist or antagonist can be subjected to further lead optimization, e.g., to further refine the structure of a lead compound so that potency and activity are maintained but balanced with important pharmacological characteristics including:
  Solubility
  Permeability
  Bioavailability
  Toxicity
  Mutagenicity
  Pharmacokinetics—absorption, distribution, metabolism, elimination of the drug Structural modifications are made to a lead compound to address issues with the parameters listed above. These modifications however, must take into account possible effects on the molecule's potency and activity. For example, if the solubility of a lead compound is poor, changes can be made to the molecule in an effort to improve solubility; these modifications, however, may negatively affect the molecule's potency and activity. SAR data are then used to determine the effect of the change upon potency and activity. Using an iterative process of structural modifications and SAR data, a balance is created between these pharmacological parameters and the potency and activity of the compound.

Candidate antagonists, or combinations thereof, must them be tested for efficacy and toxicity in animal models. Such therapeutic profiling is commonly employed in the pharmaceutical arts. Before testing an experimental drug in humans, extensive therapeutic profiling (e.g., preclinical testing) must be completed to establish initial parameters for safety and efficacy. Preclinical testing establishes a mechanism of action for the drug, its bioavailability, absorption, distribution, metabolism, and elimination through studies performed in vitro (that is, in test tubes, beakers, petri dishes, etc.) and in animals. Animal studies are used to assess whether the drug will provide the desired results. Varying doses of the experimental drug are administered to test the drug's efficacy, identify harmful side-effects that may occur, and evaluate toxicity.

Briefly, one of skill in the art will recognize that the identification of a candidate agent which antagonizes CatSper1 activity in a drug based screen is a first step in developing a pharmaceutical preparation useful as a contraceptive agent. Administration of an amount of said pharmaceutical preparation effective to successfully prevent pregnancy (i.e., to act as a useful contraceptive agent) must be both safe and effective. Early stage drug trials, routinely used in the art, help to address concerns of the safety and efficacy of a potential pharmaceutical. In the specific case of a CatSper1 antagonist, efficacy of the pharmaceutical preparation could be readily evaluated in a mouse or rat model. Briefly, male mice could be administered varying doses of said pharmaceutical preparations over various time schedules. Control male mice can be administered a placebo (e.g., carrier or excipient alone). The male mice are then allowed to mate freely by placing said male into cages with female mice, and measuring rate of conception over time. Given the efficacy of currently available forms of birth control, an effective contraception should be at least 80% effective, preferably 85% effective, more preferably 90% effective, most preferably 95%, 96%, 97%, 98%, 99% or greater than 99% effective in preventing pregnancy.

In one embodiment, the step of therapeutic profiling includes toxicity testing of compounds in cell cultures and in animals; analysis of pharmacokinetics and metabolism of the candidate drug; and determination of efficacy in animal models of diseases. In certain instances, the method can include analyzing structure-activity relationship and optimizing lead structures based on efficacy, safety and pharmacokinetic profiles. The goal of such steps is the selection of drug candidates for pre-clinical studies to lead to filing of Investigational New Drug ("ND") applications with the U.S. FDA and/or similar applications with similar regulatory authorities prior to human clinical trials.

Between lead optimization and therapeutic profiling, one goal of the subject method is to develop a CatSper1 agonist or antagonist which has minimal side-effects. In the case of antagonists, the lead compounds will have clinically acceptable effects on vasodilatation (i.e., dizziness, hypotension, headache, flushing, edema, etc.), myocardial ischemia, hypotension, bradycardia, transient asystole, exacerbation of heart failure, ventricular dysfunction, SA node or AV conduction disturbances, or plasma digoxin levels.

By "toxicity profiling" is meant the evaluation of potentially harmful side-effects which may occur when an effective amount of a pharmaceutical preparation is administered. A side-effect may or may not be harmful, and the determination of whether a side effect associated with a pharmaceutical preparation is an acceptable side effect is made during the regulatory approval process. This determination does not follow hard and fast rules, and that which is considered an acceptable side effect varies due to factors including: (a) the severity of the condition being treated, and (b) the availability of other treatments and the side-effects currently associated with these available treatments. For example, the term cancer encompasses a complex family of disease states related to mis-regulated cell growth, proliferation, and differentiation. Many forms of cancer are particularly devastating diseases which cause severe pain, loss of function of the effected tissue, and death. Chemotherapeutic drugs are an important part of the standard therapy for many forms of cancer. Although chemotherapeutics themselves can have serious side-effects including hair-loss, severe nausea, weight-loss, and sterility, such side-effects are considered acceptable given the severity of the disease they aim to treat.

In contrast, however, most currently available forms of birth control do not have significant side-effects. Thus, a pharmaceutical preparation of a CatSper1 antagonist should have minimal toxicity and side-effects. Toxicity tests can be conducted in tandem with efficacy tests, and male mice administered effective doses of the pharmaceutical preparation can be monitored for adverse reactions to the preparation. Potential adverse reactions associated with a contraceptive agent may include loss of sex drive and behavioral changes. Blood, urine, and fecal samples taken from treated mice can also be monitored to detect any potential adverse changes in immune, kidney, or liver function. Additionally, given that CatSper1 is a cation channel, mice receiving said pharmaceutical preparation should also be monitored for any changes in cardiac function indicative of cross reactivity of the CatSper1 antagonist with other cation channels.

Agents which antagonize CatSper1 activity, and which are proven safe and effective in animal studies, can be formulated into a pharmaceutical preparation. Such pharmaceutical preparations can then be marketed, distributed, and sold as contraceptive agents.

Given the link between loss of CatSper1 activity and fertility, there is substantial utility in agents which increase the activity of CatSper1 to treat male fertility problems. Many instances of infertility involve problems linked to the male. Such male infertility issues include low sperm count, poor sperm motility, and abnormal sperm morphology. Currently there are few effective treatments for male-associated infertility.

The first step in developing potentially successful treatments for male infertility is the identification of CatSper1 agonists. A CatSper1 agonist is one or more agents which increase the activity of CatSper1. As outlined in detail above for CatSper1 antagonists, agonists of the CatSper1 protein are expected to have fewer potential side-effects than other cation channel agonists.

Methods for identifying agents which act as CatSper1 agonists are performed largely as detailed for CatSper1 antagonists. However, a preferred CatSper1 agonist will increase one or more of sperm motility or egg penetrance. Additionally, we note that when identifying a CatSper1 agonist, such an agent may agonize the activity of a wild type CatSper1. In addition, or alternatively, such an agent may agonize the activity of a mutant CatSper1. One or more agonists identified by these methods can then be tested for safety and efficacy, as outline in detail above. Agents which are shown to be safe and effective in animal studies are formulated into a pharmaceutical preparation.

We note that said CatSper1 agonists are not likely to be effective for treating all male fertility problems. However, it is expected that some undetermined percentage of male fertility problems will be amenable to treatment using agonists of CatSper1 function. For example, a certain percentage of male infertility which results in poor sperm motility is likely due to mutations in CatSper1. Given that CatSper1 is expressed specifically in sperm, males possessing such a mutation would be expected to have little or no additional medical problems, and this explains in part why infertility is often found in otherwise healthy men. Additionally, a CatSper1 agonist may improve sperm motility overall, and thus help compensate for poor sperm motility due to other unrelated causes.

Conducting a Reproductive Medicine Business.

A pharmaceutical preparation including one or more agents which agonize the activity of a wild type or mutant CatSper1 may be useful in establishing a reproductive medicine business which provides treatment for candidate male patients experiencing fertility difficulties. Sperm samples provided by male patients are examined to determine if infertility in said male patients may be amenable to treatment with the pharmaceutical preparation. Patients whose sperm is characterized by a decrease in at least one of motility or egg penetrance may be eligible for treatment. Prior to treatment, sperm samples provided by the male patients are tested in vitro with the pharmaceutical preparation to further assess whether said male is eligible for treatment. This additional step of in vitro testing helps to alleviate unnecessary treatment in males whose infertility is unlikely to be improved with the CatSper1 agonist.

Male patients whose sperm shows increased motility or egg penetrance in vitro are eligible for fertility treatment including the pharmaceutical preparation including one or more CatSper1 agonist. The exact treatment regimen will vary from patient to patient, and can be readily determined by an experienced medical professional. However, the treatment regimen will include administration of an amount of said pharmaceutical preparation effective to increase at least one of sperm motility or egg penetrance in said treated male. In a preferred embodiment, the increase in sperm motility or egg penetrance will result in an increase in fertility.

Pharmaceutical Preparations.

Pharmaceutically acceptable preparations comprising a therapeutically effective amount of one or more of the identified agents (i.e., antagonists or agonists) described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The phrase "therapeutically effective amount" as used herein means that amount of an agent or composition which is effective for producing some desired therapeutic effect, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, the pharmaceutical preparation is non-pyrogenic, i.e., does not elevate the body temperature of a patient.

The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977), J. Pharm. Sci. 66: 1-19.)

The pharmaceutically acceptable salts of the subject agents include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the agents of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al. (1977), supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1% to about 99% of active ingredient, preferably from about 5% to about 70%, most preferably from about 10% to about 30%.

Methods of preparing these formulations or compositions include the step of bringing into association one or more agents of the present invention with the carrier and, optionally, one or more accessory ingredients. In general, the formulations are prepared by uniformly and intimately bringing into association one or more agents of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A agent of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more agents of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of one or more agents of this invention include powders, sprays, ointments, pastes, creams, lotions, gels, solutions, patches and inhalants. The active agents may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an agent of the present invention to the body. Such dosage forms can be made by dissolving or dispersing the subject compound in the proper medium. Absorption enhancers can also be used to increase the flux of the subject agent across the skin. The rate of such flux can be controlled by either providing a rate controlling membrane or dispersing the compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The following examples illustrate some preferred modes of practicing the present invention, but are not intended to limit the scope of the claimed invention. Alternative materials and methods may be utilized to obtain similar results.

Example 1

Cloning of Human and Murine CatSper1 Genes

A fragment of an EST cDNA (accession number AA416682) that showed similarity to known high voltage-gated $Ca^{2+}$ channels was identified during a database search for novel $Ca^{2+}$ channels. Primers derived from this sequence were used to perform RT/PCR to obtain a cDNA fragment. The fragment was used as a probe to localize the main source of expression in testis (see below). cDNA library screening and RACE were used to clone the cDNAs containing the whole open reading frame (ORF) from human and mouse testes. The start of the ORF was confirmed by an in-frame stop codon upstream of the first ATG. The ORF of the CatSper1 gene encodes a primary structure of 686 amino acids (FIG. 1a). cDNA constructs for expression in mammalian cells were made by PCR using Pfu polymerase. The constructs were completely sequenced and contained no mutations. Northern and dot blots were from Clontech (Palo Alto, Calif.).

Figures 1, 5A:
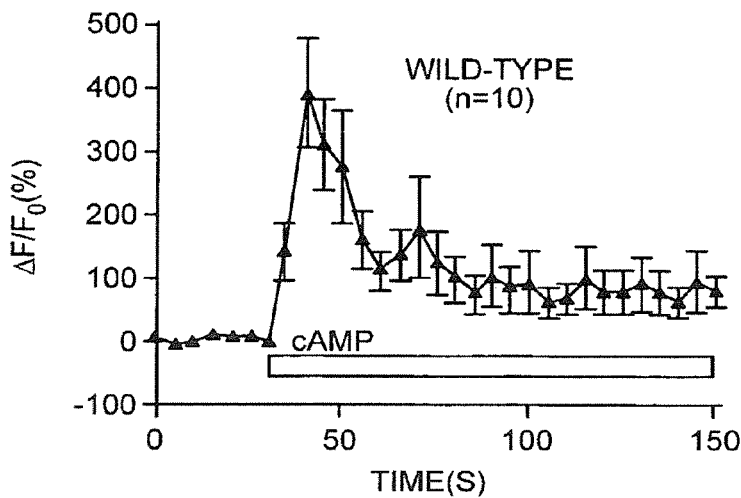
FIG. 1 shows the primary structure of mouse CatSper1. (a) Amino acid sequence (SEQ ID NO: 4); the 6 putative transmembrane domains (S1-S6) and the pore (P) region are boxed. The positively charged residues (K/R) in the S4 region are shown in bold. (b) Hydropathy plot of CatSper1 predicts 6 transmembrane domains (1-6) and a P loop (P). Window size=11. (c) Alignment of the putative pore region of CatSper1 with that of the four domains (I, II, III, IV) from $Ca_V1$-3. GenBank accession numbers: X15539 ($Ca_V1.2$) (SEQ ID NOs 8, 11, 14 and 17, respectively, in order of appearance), M94172 ($Ca_V2.2$) (SEQ ID NOs 9, 12, 15 and 18, respectively, in order of appearance), O54898 ($Ca_V3.1$) (SEQ ID NOs 10, 13, 16 and 19, respectively, in order of appearance), AF407332 (mouse CatSper1) (SEQ ID NO: 7), and AF407333 (human CatSper1) (SEQ ID NO: 20).

In a BLAST search, the functional proteins with closest similarity to CatSper1 were voltage-gated $Ca^{2+}$ channels, not Kv, cyclic nucleotide-gated (CNG), or transient receptor potential (TRP) channels. The pore-forming subunits ($\alpha_1$) of $Ca_V$ channels have four repeats of 6 transmembrane-spanning domains (Ertel, et al. (2000), Neuron 25, 533-5). Located in the putative channel pore region of each of the four repeats are glutamine/aspartate residues that impart $Ca^{2+}$ selectivity on the channel by coordinating $Ca^{2+}$ ions (Ellinor, et al. (1995), Neuron 15, 1121-32). These residues are conserved among all the established $Ca_V$ channels and CatSper1 (FIG. 1c). As is characteristic for voltage-gated channels, positively charged amino acids (K/R) are interspersed every three amino acids in the transmembrane region of the putative CatSper1 S4 domain. Like $K_V$, CNG, and TRP channels, a hydrophobicity plot of CatSper1 (FIG. 1b) predicted that it contained 6 transmembrane-spanning domains. CatSper1 contains a remarkable abundance of histidine residues in its amino-terminus (49/250 amino acids), which could play a role in the well-known pH regulation of sperm motility (Yanagimachi (1994), in The Physiology of Reproduction, eds. Knobil & Neill (Raven Press, New York), pp. 189-315). Human CatSper1 exhibited a high degree of homology (55% identity/72% similarity) with its mouse counterpart, especially in the transmembrane domains and the histidine-rich region. In the transmembrane domains there was 81% identity/93% similarity and in the pore region, 89% identity/100% similarity. Low stringency screening of a mouse testis cDNA library with human CatSper1 revealed no other genes of higher similarity.

Example 2

Cellular Localization of CatSper1

CatSper1 mRNA was detected in testis as a single ~2.6 kb band. The size of the mRNA was similar to that of the cDNA clones that had been isolated, suggesting that the gene product was a full-length transcript and not a truncated form of a much larger conventional $Ca_V$ channel. CatSper1 mRNA was detected only in testis when examined in 8 mouse tissues (heart, grain, spleen, lung, liver, skeletal muscle, kidney and testis) and 16 human tissues (pancreas, kidney, skeletal muscle, liver, lung, placenta, brain, heart, spleen, thymus, prostate, ovary, small intestine, colon mucosal lining, peripheral blood leukocytes, and testis). Furthermore, a CatSper1 mRNA probe recognized only testis in a dot blot of 50 human tissue mRNAs (whole brain, amygdala, caudate nucleus, cerebellum, cerebral cortex, frontal lobe, hippocampus, medulla oblongata, occipital lobe, putamen, substantia nigra, temporal lobe, thalamus, nucleus accumbens, spinal cord, heart, aorta, skeletal muscle, colon, bladder, uterus, prostate, stomach, testis, ovary, pancreas, pituitary gland, adrenal gland, thyroid gland, salivary gland, mammary gland, kidney, liver, small intestine, spleen, thymus, peripheral leukocyte, lymph node, bone marrow, appendix, lung, trachea, placenta, fetal brain, fetal heart, fetal kidney, fetal liver, fetal spleen, fetal thymus, fetal lung).

A polyclonal antibody directed against the first 150 amino acids of the amino terminus recognized the CatSper1 protein. The antibody specifically labeled tetracycline-induced CatSper1 proteins from HEK-293 cells and native CatSper1 in testis, sperm, and spermatocytes. Consistent with the results of the Northern blots, the antibody did not recognize similar size proteins from brain, heart, or kidney.

Indirect immunofluorescence revealed the subcellular localization of sperm CatSper1. The protein was strikingly localized to the principal piece of the sperm tails. CatSper1 was presumably localized to the plasma membrane since the principal piece does not contain intracellular organelles (e.g., endoplasmic reticulum). In order to determine the precise location of the protein in the sperm tail, indirect immunogold electron microscopy was performed. CatSper1 immunoreactive gold particles were detected in the plasma membrane above the fibrous sheath in the sperm principal piece. Consistent with the immunofluorescence staining, few immunoreactive gold particles were detected in either the head or midpiece. The detection of gold particles on the cytoplasmic face of the plasma membrane supports the predicted intracellular localization of CatSper1's amino terminus.

Example 3

Targeted Disruption of CatSper1

Figures 2, 5A:
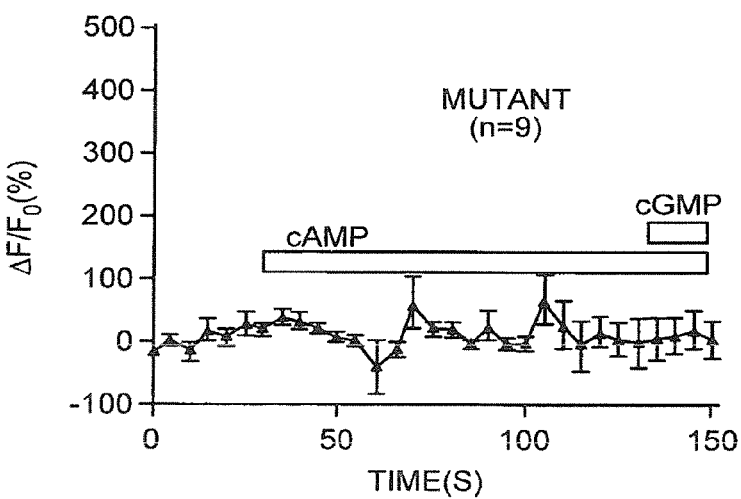
FIG. 2 shows the partial genomic structure of mouse CatSper1 gene and the targeting vector used for targeted disruption of the CatSper1 gene. Exons are shown as filled boxes; introns as thinner lines.

The CatSper1 gene was disrupted in murine embryonic stem (ES) cells by homologous recombination in order to study its function in vivo. Genomic BAC clones containing the CatSper1 gene were isolated and analyzed by restriction digestion and sequencing. A targeting vector (FIG. 2) was constructed to contain 5 kb of the CatSper1 5' sequence (left arm), IRES-LacZ followed by a Neo-resistant gene (middle), and 1.7 kb of the CatSper1 3' sequence followed by TK as a negative selection marker (right arm). Thus, the second exon encoding the first putative transmembrane domain was replaced with an IRES-LacZ sequence followed by the neomycin-resistance gene. To generate chimeras, ES cells derived from 129/SvJ mice were transfected with linearized DNA, selected, and analyzed for correct targeting. Correctly targeted ES cells carrying a mutant copy of the gene were injected into blastocysts and implanted in pseudo-pregnant mice. Chimeric mice were crossed with C57BU6J to obtain heterozygous mutants, and fully mutant mice were generated from the mating of offspring. Disruption of the gene was confirmed by PCR, Western blotting, immunostaining and immunogold electron microscopy. Mice used in the study were the offspring of crosses between F1 and/or F2 generations (129/SvJ/C57BU6J genetic background). Wild-type littermates were used as controls in the IVF experiments.

Example 4

Role of CatSper1 in Male Fertility

The genotypes of heterozygous (+/−) males and female offspring exhibited roughly Mendelian proportions (240+/−; 106+/+; 110−/−), suggesting that the mutation did not affect embryonic development. The CatSper1$^{-/-}$ (mutant) mice were indistinguishable from their wild-type littermates in survival rates, appearance, and gross behavior.

Homozygous (−/−) females mated with heterozygous (+/−) or wild-type (+/+) males were fertile. Homozygous male mutants mated with wild-type females displayed mounting behavior indistinguishable from that of wild-type males. The similar frequencies of vaginal plugs noted in mated females supported the normal mating behavior of wild-type and mutant mice. However, the mutant males engendered no pregnancies over a period greater than 2 months (up to 9 months; n=26 females; 13 males). In contrast, the wild-type littermate males were 100% fertile (n=8 females; 4 males; FIG. 3a).

Figure 3B:
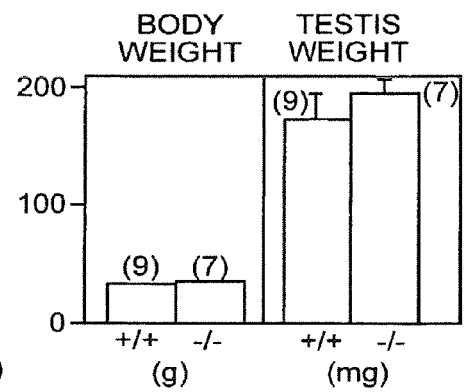
Figure 3C:
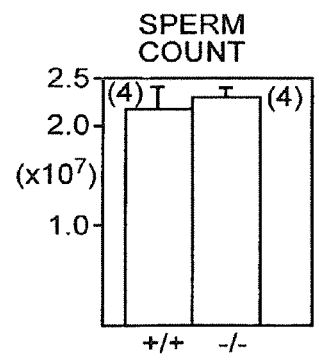

Body and testis weights of the mutant mice were not different from those of the wild-type counterparts (FIG. 3b). Sperm counts from mutant and wild-type caudal epididymis were not significantly different and the sperm were cytologically indistinguishable (FIG. 3c). The absence of spermatogenesis defects in CatSper1$^{-/-}$ mice was supported by the lack of morphological differences between wild-type and mutant mouse testes.

Figure 3D:
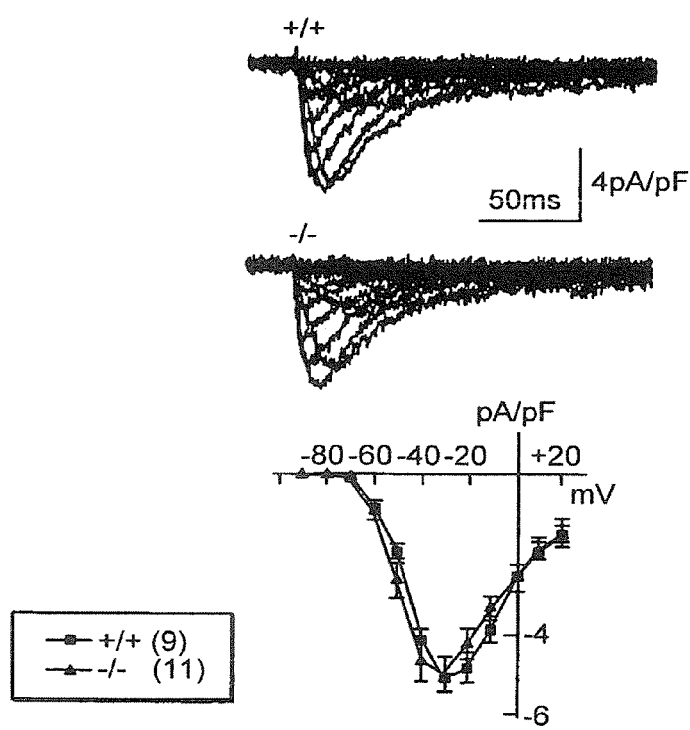

A major effort was made to determine the precise electrophysiological characteristics of the wild-type and mutant sperm. As detailed below, hundreds of attempts to measure whole-cell currents of both wild-type and mutant sperm under a variety of conditions and configurations were unsuccessful, consistent with the experience of other investigators. However, the voltage-gated $Ca^{2+}$ channel currents from mutant and wild-type spermatocytes were successfully recorded. The measured $Ca^{2+}$ currents were consistent with previous data (Santi, et al. (1996), *Am J Physiol* 271, C1583-93; Arnoult, et al. (1996), *Proc Natl Acad Sci USA* 93, 13004-9), and no significant differences between wild-type and mutant mouse spermatocyte inward currents were detected (FIG. 3d). No inward currents were induced by cyclic nucleotides in wild-type or mutant spermatocytes. Thus, CatSper1 was not a major component of the spermatocyte voltage-sensitive $Ca^{2+}$ currents and was not required for the development of sperm from spermatocytes.

Example 5

Role of CatSper1 in Normal Sperm Motility

Figure 4A:
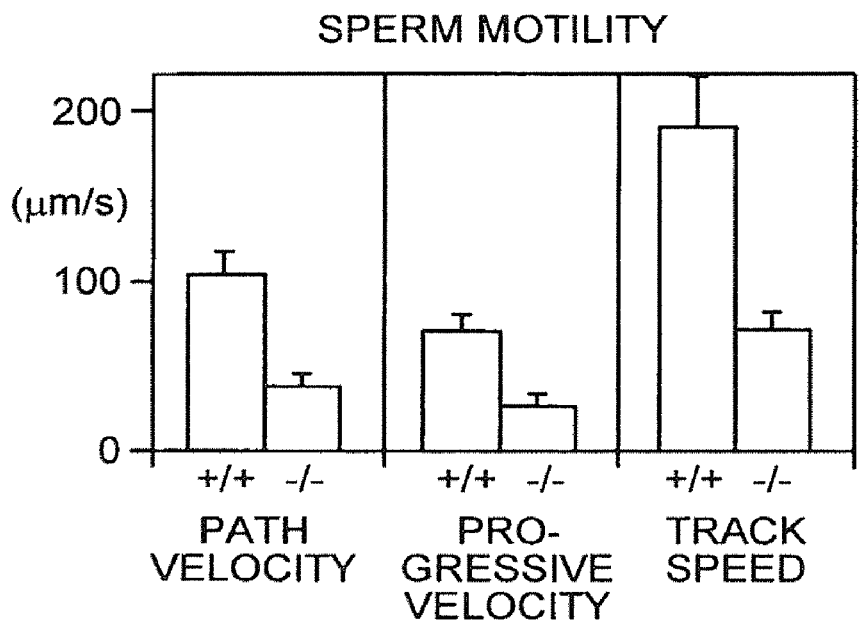
FIG. 4 shows CatSper1$^{-/-}$ sperm motility and in vitro fertilization defects. (a) Path velocity, progressive velocity and track speed quantitated sperm motility. (b) In vitro fertilization (IVF) rates of mutant and the wild-type sperm with ZP-intact and ZP-free ova (3 pairs of mutant and wild-type mice each).

A closer examination of live sperm under light-microscopy revealed a significant difference between the mutant and wild-type sperm. Sperm from wild-type mice displayed vigorous beating in the tail region and progressive directed movement. CatSper1$^{-/-}$ sperm were sluggish and displayed less directed movements. Most strikingly, mutant sperm lacked the vigorous beating and bending in the tail region. Computer Assisted Sperm Analysis (CASA) revealed that the mutant sperms' major motility parameters of path velocity, progressive velocity, and track speed were significantly impaired (FIG. 4a). Thus disruption of the CatSper1 gene resulted in dramatically reduced sperm motility.

Example 6

Sperm Require CatSper1 to Penetrate the Ova's Extracellular Matrix

Figure 4B:
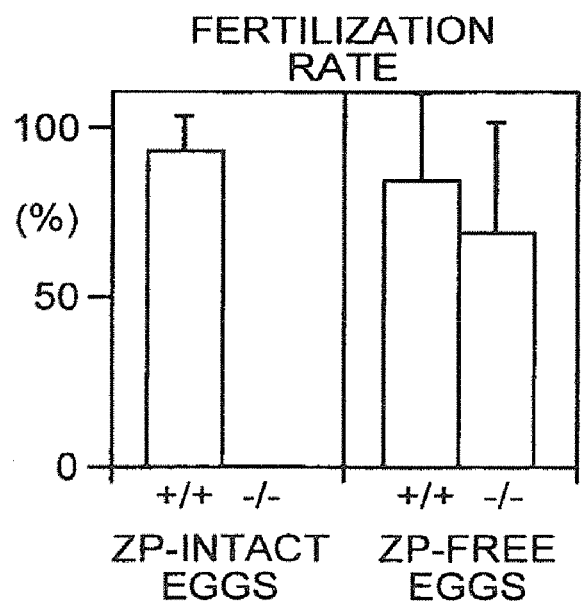

In vitro fertilization (IVF) assays were performed to test CatSper1$^{-/-}$ sperm's ability to fertilize ova. Sperm were collected from cauda epididymis and capacitated in vitro for 2 h. Ova were collected from mature wild-type females (~6 weeks old) synchronized with 10 units PMSG and 10 units hCG, 46-48 h and 14 h before collection, respectively. IVF was performed using standard protocols (Perez, et al. (1999), *Nat Genet* 21, 200-3). Ova were incubated with ~$10^5$ CatSper1+/+ or CatSper1$^{-/-}$ sperm for 4 h at 37° C. and unbound sperm were washed away. After 20 h incubation at 37° C., ova were examined for the presence of the 2-cell stage embryos as an indication of successful fertilization. While 81% of ova (66/81) were fertilized by the wild-type sperm, no ova (0/79) were fertilized by the CatSper1$^{-/-}$ sperm (FIG. 4b). Ova fertilized by wild-type sperm developed into two-cell stage embryos while ova incubated with the mutant sperm remained at the single cell stage. Some CatSper1$^{-/-}$ sperm adhered to the ova but did not appear to be able to penetrate the ova, possibly due to impaired motility. Some embryos were fixed and stained with Hoechst 33342 for imaging immediately after IVF.

During the course of natural fertilization, sperm penetrate the surrounding layer of ZP proteins and fuse to the ovum plasma membrane. To examine whether the mutant sperm retained the ability to fuse with the plasma membrane and activate fertilization, wild-type and mutant sperm were incubated with ova whose outer layers were enzymatically removed (ZP-free ova) by treating with hyaluronidase (80 IU/ml) followed by perfusion in Tyrode's solution for 30-40 seconds. Under such conditions, sperm from both the CatSper1$^{+/+}$ and CatSper1$^{-/-}$ mice were capable of fertilizing the ova (FIG. 4b). Thus, CatSper1 is required for the sperm to be able to penetrate the ovum outer layers, but not for ovum activation.

Example 7

CatSper1 is Required for cAMP-Induced Ca$^{2+}$ Influx

For electrophysiology measurements, spermatocyte preparation and whole-cell current recording were performed essentially as previously described (Santi, et al. (1996), *Am J Physiol* 271, C1583-93; Arnoult, et al. (1997), *EMBO J.* 16, 1593-9). The pipette solution contained (in mM): 120 Cs$^+$, 60 glutamic acid, 20 TEA-Cl, 5 MgCl$_2$, 3 Mg-ATP, 10 EGTA, 10 HEPES and 5 D-glucose (pH 7.4). The bath contained (in mM): 135 NaCl, 5 KCl, 10 CaCl$_2$, 10 Na-lactate, 10 Na-pyruvate, 10 glucose and 30 HEPES (pH 7.4). Leak currents were subtracted using an online P/4 protocol. The data were filtered at 1 kHz. Data were corrected for junction potentials.

For Ca$^{2+}$ imaging, sperm were prepared in HS medium (Wennemuth, et al. (2000), *J Biol Chem* 275, 21210-7) and loaded with 10 µM Fluo-4-AM and 0.05% Pluronic F-127 for 30 min. at room temperature. Washed cells were seeded onto Cell-Tak coated cover slips. Attached motile sperm were imaged in nonconfocal mode to avoid motion-induced fluorescence change artifacts. The 488 nm wavelength beam of an Argon-Krypton laser was used for excitation and fluorescence emission was collected at 512 nm (Zeiss LSM 410).

Cyclic nucleotides have been widely implicated in sperm motility (Tash (1990) in *Controls of Sperm Motility: biological and clinical aspects*, ed. Gagnon (CRC Press, Boca Raton), pp. 229-240; Darszon, et al. (1999), *Physiol Rev* 79, 481-510, *Physiol Rev* 79,481-510; Hyne & Garbers (1979), *Proc Natl Acad Sci USA* 76, 5699-703; Aoki, et al. (1999), *Mol Reprod Dev* 53, 77-83). To elucidate the function of CatSper1, the mouse and human CatSper1 were expressed in various heterologous expression systems including *Xenopus* oocytes, HEK-293 and CHO-K1 cells. In over 250 patch clamp studies, significant current was not detected as a result of CatSper1 expression, alone or in combination with expressed CNG α channel subunits (CNG4 or CNG6). While CatSper1 protein could be detected in the expression system, no currents could be elicited by changes in voltage, pH, osmolarity, and/or cyclic nucleotide concentration. As a positive control, cyclic nucleotide-activated channel currents were measured after expression of the CNG α subunit (CNG1) and β subunit (CNG6). Attempts were also made to compare the currents of wild-type and mutant sperm head and tail membranes. As reported by others (Espinosa, et al. (1998), *FEBS Lett* 426, 47-51), the success rate for obtaining stable patches from sperm was very low, presumably due to the small diameter (0.5 µm) and the geometry of sperm tails. Of ~900 attempts under various conditions, fewer than 30 gigaseals were formed and none were stable whole-cell recordings. Although no differences between wild-type and mutant cell-attached patches were noted, the low success rate prevented any reliable analysis. Therefore, sperm tail intracellular Ca$^{2+}$ dynamics, which could be readily monitored with Ca$^{2+}$ indicators (Wiesner, et al. (1998), *J Cell Biol* 142, 473-84; Kobori, et al. (2000), *Biol Reprod* 63, 113-20), were examined.

Figure 5B:
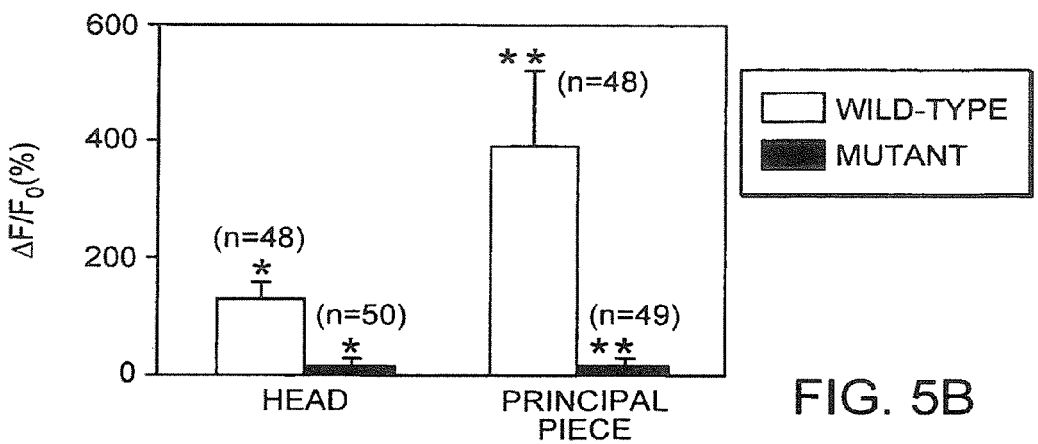
FIG. 5 shows a summary of cyclic nucleotide-induced $Ca^{2+}$ changes. (a) Time courses of the cAMP-induced $Ca^{2+}$ changes in wild-type (CatSper1$^{+/+}$) and mutant (CatSper1$^{-/-}$) sperm principal pieces. (b) Mean fluorescence change in sperm heads and principal pieces from CatSper1$^{+/+}$ and CatSper1$^{-/-}$ mice. Fluorescence was normalized to the average of the first 7 sampling points of the prestimulation trace.

Wild-type and mutant sperm were loaded with Fluo-4 and their fluorescence measured by single photon confocal microscopy. Application of cell membrane-permeant cAMP (1 mM 8-Br-cAMP) to the bath containing caudal epididymal wild-type sperm initiated a rapid rise in sperm head and tail [Ca$^{2+}$]$_i$ (FIG. 5). This [Ca$^{2+}$]$_i$ signal was not detected in Ca$^{2+}$-free bath medium, suggesting that Ca$^{2+}$ influx was mediated by a plasma membrane channel. Membrane permeant cyclic GMP (1 mM 8-Br-cGMP) also initiated Ca$^{2+}$ influx in sperm. The cyclic AMP and cyclic GMP induced [Ca$^{2+}$]$_i$ increase was not blocked by incubating sperm with the nonspecific kinase inhibitor staurosporine (1 µM, 10 minutes), suggesting that cyclic nucleotide dependent protein kinases are not essential for channel activation. Addition of sodium bicarbonate to the bath (20 mM), a physiologically relevant stimulus to sperm (Hyne & Garbers (1979), *Proc Natl Acad Sci USA* 76, 5699-703), induced an increase in [Ca$^{2+}$]$_i$ that was smaller than that observed with cyclic AMP or GMP. A significant cyclic nucleotide-induced [Ca$^{2+}$]$_i$ rise was also detected in testis-derived sperm but not in spermatids (nor in developing elongated spermatids with short tails), suggesting that the Ca$^{2+}$ response to cAMP is a property of the fully differentiated sperm. In CatSper1$^{-/-}$ sperm, neither cAMP nor cGMP elicited significant Ca$^{2+}$ influx (FIG. 5). As a control for sufficient dye loading, progesterone initiated a large Ca$^{2+}$ influx in both the mutant and the wild-type sperm. Thus, CatSper1 is required for the cAMP- and cGMP-induced Ca$^{2+}$ influx in sperm.

Example 8

Antibodies and Immunostaining

Affinity-purified polyclonal antibody was generated against a GST fusion protein of the N-terminal 150 amino acids. Western blots were carried out with 2 µg/ml anti-CatSper1 antibody. Immunostaining with 5 µg/ml anti-CatSper1 antibody was detected with a rhodamine-conjugated anti-rabbit secondary antibody. Ten µg/ml of anti-CatSper1 antibody and 10 nm gold-conjugated protein A were used in immuno-EM; 60 nm sections were cut from embedded cells. CatSper1$^{-/-}$ sperm were used as controls in all the experiments to ensure the specificity of the antibodies.

EQUIVALENTS

While this invention has been particularly shown and described with references to preferred embodiments thereof, it will be understood by those skilled in the art that various changes in form and details may be made therein without departing from the spirit and scope of the invention. Those skilled in the art will recognize, or be able to ascertain using no more than routine experimentation, many equivalents to the specific embodiments of the invention described specifically herein. Such equivalents are intended to be encompassed in the scope of the invention.

We claim:

1. An isolated nucleic acid comprising:
   (a) a nucleotide sequence encoding a CatSper1 protein comprising SEQ ID NO: 2; or
   (b) the nucleotide sequence complementary to the nucleotide sequence of (a).

2. The isolated nucleic acid of claim 1, wherein said nucleotide sequence encoding a CatSper1 protein comprises SEQ ID NO: 1.

3. The isolated nucleic acid of either claim 1 or claim 2, further comprising:
   a heterologous regulatory region operably joined to said sequence.

4. A vector comprising an isolated nucleic acid of claim 3.

5. An isolated cell transformed with the vector of claim 4.

6. An isolated cell transformed with the nucleic acid of claim 3.

7. A kit for detecting a CatSper1 nucleic acid comprising a container comprising:
   an isolated nucleic acid of either claim 1 or claim 2; and
   a means for detecting said isolated nucleic acid.

8. The kit of claim 7, wherein
   said means for detecting said isolated nucleic acid comprises a detectable label bound thereto.

9. The kit of claim 7, wherein
   said means for detecting said isolated nucleic acid comprises a labeled secondary nucleic acid which specifically hybridizes to said isolated nucleic acid.

10. A vector comprising an isolated nucleic acid of either claim 1 or claim 2.

11. An isolated cell transformed with the vector of claim 10.

12. An expression vector comprising a genetic construct capable of expressing a nucleic acid of either claim 1 or claim 2.

13. The vector of claim 12, wherein said nucleic acid is operably joined to a heterologous regulatory region.

14. An isolated cell transformed with the vector of claim 13.

15. The vector of claim 12, wherein said nucleic acid is operably joined to heterologous coding sequences.

16. An isolated cell transformed with the vector of claim 15.

17. An isolated cell transformed with the vector of claim 12.

18. A vector comprising an isolated nucleic acid of either claim 1 or claim 2 operably joined to a reporter gene.

19. An isolated cell transformed with the vector of claim 18.

20. An isolated cell transformed with the nucleic acid of either claim 1 or claim 2.

21. The isolated cell of claim 20, wherein
   said cell is selected from the group consisting of bacterial cells, yeast cells, insect cells, nematode cells, amphibian cells, rodent cells, and human cells.

22. The isolated cell of claim 20, wherein
   said cell is selected from the group consisting of mammalian somatic cells, fetal cells, embryonic stem cells, zygotes, gametes, germ line cells, and transgenic animal cells.

* * * * *

SEQUENCE LISTING

<160> NUMBER OF SEQ ID NOS: 20

<210> SEQ ID NO 1
<211> LENGTH: 2343
<212> TYPE: DNA
<213> ORGANISM: Homo sapiens

<400> SEQUENCE: 1

```
atggatcaaa actcagtgcc tgaaaaggct cagaatgagg cagacaccaa taacgcagat      60
aggttctttc gctctcactc atcacccca caccacaggc caggccacag cagagctctc     120
caccattacg agttgcacca tcacggcgtg ccccaccaac gtggtgaatc tcaccaccct     180
ccggagttcc aagacttcca cgaccaagcc ttgtcctccc atgtccacca atctcaccac     240
cacagcgagg cacggaatca cggcagagcc catggcccca caggctttgg tctggctccc     300
tctcaaggcg ccgtccctc ccaccgttcc tacggtgagg actaccatga tgagctccaa     360
cgtgatggca ggaggcatca tgatgggtcc caatacggtg ggttccatca gcagagtgac     420
tcccattacc atagggggtc tcaccatggc agaccccaat atctcggtga aatttatcc     480
cactattcct ctggcgtgcc ccaccacggt gaggcttccc accatggtgg gtcctacctc     540
ccccatggac ccaatcccta cagtgagtcc ttccaccaca gcgaggcttc ccaccttagc     600
gggctccaac acgatgagtc ccagcatcac caagtccccc accgtggctg ccccaccat     660
caccaagtcc accaccatgg caggtcccgt catcatgaag cccaccagca tggaaagtct     720
cctcatcacg gagagaccat ttcccctcat tcctctgtgg ggtcctacca gcgtgggata     780
tctgactatc acagcgagta ccaccaaggt gatcaccacc ccagtgagta ccaccatggc     840
gaccatcccc accacacaca gcaccactac caccagaccc accggcaccg agactaccat     900
cagcaccaag accaccacgg cgcgtatcat tccagttacc tccatggcga ctacgtccag     960
agcacttccc aactctctat cccacacaca tcccggagcc tgattcacga tgccccggc    1020
cctgctgctt ctcgtacagg agtcttcccc tatcacgtag cacacccacg gggctcggct    1080
cacagcatga ctcggtcctc cagcacaatc cgctcacgtg tcacccagat gtccaaaaaa    1140
gtccatacc aggatatctc caccaaaacat tcagaagact ggggcaaaga agaagggcaa    1200
tttcagaaac gcaaaaccgg caggctccag cggacccgca agaagggaca ctctaccaat    1260
ctcttccagt ggctgtggga aaagctaacc ttcctcattc agggcttccg ggaaatgatc    1320
cggaacctga cccaatcctt ggcctttgaa actttcatct tcttcgttgt ctgcctcaac    1380
accgtcatgc tggtggccca gaccttcgct gaagtcgaga tccggggcga gtggtacttc    1440
atggccttgg actccatatt cttctgcatc tacgtggtgg aagccctgct caagatcatc    1500
gccctgggcc tctcgtactt ctttgacttc tggaacaatt tggacttctt cattatggcc    1560
atggccgtgc tggacttctt gctgatgcag acccactcct tcgccatcta ccaccaaagc    1620
ctcttccgga tcctcaaggt cttcaagagc ctgcgggccc tgagggcaat ccgggtcctg    1680
cggaggctca gcttcctgac cagcgtccag gaagtgacag ggaccctggg ccagtccttg    1740
ccgtccatcg cagccatcct catcctcatg tttacctgcc tcttcctctt ctccgcggtc    1800
ctccgggcac tgttccgcaa atctgacccc aagcgcttcc agaacatctt caccaccatc    1860
ttcaccctct tcaccttgct cacgctggat gactggtccc tcatctacat ggacagccgt    1920
gcccagggcg cctggtacat cattcccatc ctcataattt acatcatcat ccagtacttc    1980
atcttcctca acctggtgat tactgtcctg gtggatagct tccagacggc gctgttcaaa    2040
```

-continued

```
ggccttgaga aagcgaagca ggagagggcc gcccggatcc aagagaagct gctggaagac    2100
tcactgacgg agctcagagc tgcagagccc aaagaggtgg cgagtgaagg caccatgctg    2160
aagcggctca tcgagaaaaa gtttgggacc atgactgaga agcagcagga gctcctgttc    2220
cattacctgc agctggtggc aagcgtggag caggagcagc agaagttccg ctcccaggca    2280
gccgtcatcg atgagattgt ggacaccaca tttgaggctg agaagagga cttcaggaat    2340 tga                                                                   2343
```

<210> SEQ ID NO 2
<211> LENGTH: 780
<212> TYPE: PRT
<213> ORGANISM: Homo sapiens

<400> SEQUENCE: 2

```
Met Asp Gln Asn Ser Val Pro Glu Lys Ala Gln Asn Glu Ala Asp Thr
1               5                   10                  15

Asn Asn Ala Asp Arg Phe Phe Arg Ser His Ser Pro Pro His His
            20                  25                  30

Arg Pro Gly His Ser Arg Ala Leu His His Tyr Glu Leu His His His
        35                  40                  45

Gly Val Pro His Gln Arg Gly Glu Ser His His Pro Pro Glu Phe Gln
    50                  55                  60

Asp Phe His Asp Gln Ala Leu Ser Ser His Val His Gln Ser His His
65                  70                  75                  80

His Ser Glu Ala Arg Asn His Gly Arg Ala His Gly Pro Thr Gly Phe
                85                  90                  95

Gly Leu Ala Pro Ser Gln Gly Ala Val Pro Ser His Arg Ser Tyr Gly
            100                 105                 110

Glu Asp Tyr His Asp Glu Leu Gln Arg Asp Gly Arg His His Asp
        115                 120                 125

Gly Ser Gln Tyr Gly Gly Phe His Gln Gln Ser Asp Ser His Tyr His
    130                 135                 140

Arg Gly Ser His His Gly Arg Pro Gln Tyr Leu Gly Glu Asn Leu Ser
145                 150                 155                 160

His Tyr Ser Ser Gly Val Pro His Gly Glu Ala Ser His Gly
                165                 170                 175

Gly Ser Tyr Leu Pro His Gly Pro Asn Pro Tyr Ser Glu Ser Phe His
            180                 185                 190

His Ser Glu Ala Ser His Leu Ser Gly Leu Gln His Asp Glu Ser Gln
        195                 200                 205

His His Gln Val Pro His Arg Gly Trp Pro His His His Gln Val His
    210                 215                 220

His His Gly Arg Ser Arg His His Glu Ala His Gln His Gly Lys Ser
225                 230                 235                 240

Pro His His Gly Glu Thr Ile Ser Pro His Ser Ser Val Gly Ser Tyr
                245                 250                 255

Gln Arg Gly Ile Ser Asp Tyr His Ser Glu Tyr His Gln Gly Asp His
            260                 265                 270

His Pro Ser Glu Tyr His His Gly Asp His Pro His Thr Gln His
        275                 280                 285

His Tyr His Gln Thr His Arg His Arg Asp Tyr His Gln His Gln Asp
    290                 295                 300

His His Gly Ala Tyr His Ser Ser Tyr Leu His Gly Asp Tyr Val Gln
305                 310                 315                 320
```

```
Ser Thr Ser Gln Leu Ser Ile Pro His Thr Ser Arg Ser Leu Ile His
            325                 330                 335

Asp Ala Pro Gly Pro Ala Ala Ser Arg Thr Gly Val Phe Pro Tyr His
            340                 345                 350

Val Ala His Pro Arg Gly Ser Ala His Ser Met Thr Arg Ser Ser Ser
            355                 360                 365

Thr Ile Arg Ser Arg Val Thr Gln Met Ser Lys Lys Val His Thr Gln
            370                 375                 380

Asp Ile Ser Thr Lys His Ser Glu Asp Trp Gly Lys Glu Glu Gly Gln
385                 390                 395                 400

Phe Gln Lys Arg Lys Thr Gly Arg Leu Gln Arg Thr Arg Lys Lys Gly
            405                 410                 415

His Ser Thr Asn Leu Phe Gln Trp Leu Trp Glu Lys Leu Thr Phe Leu
            420                 425                 430

Ile Gln Gly Phe Arg Glu Met Ile Arg Asn Leu Thr Gln Ser Leu Ala
            435                 440                 445

Phe Glu Thr Phe Ile Phe Phe Val Val Cys Leu Asn Thr Val Met Leu
            450                 455                 460

Val Ala Gln Thr Phe Ala Glu Val Glu Ile Arg Gly Glu Trp Tyr Phe
465                 470                 475                 480

Met Ala Leu Asp Ser Ile Phe Phe Cys Ile Tyr Val Val Glu Ala Leu
            485                 490                 495

Leu Lys Ile Ile Ala Leu Gly Leu Ser Tyr Phe Phe Asp Phe Trp Asn
            500                 505                 510

Asn Leu Asp Phe Phe Ile Met Ala Met Ala Val Leu Asp Phe Leu Leu
            515                 520                 525

Met Gln Thr His Ser Phe Ala Ile Tyr His Gln Ser Leu Phe Arg Ile
            530                 535                 540

Leu Lys Val Phe Lys Ser Leu Arg Ala Leu Arg Ala Ile Arg Val Leu
545                 550                 555                 560

Arg Arg Leu Ser Phe Leu Thr Ser Val Gln Glu Val Thr Gly Thr Leu
            565                 570                 575

Gly Gln Ser Leu Pro Ser Ile Ala Ala Ile Leu Ile Leu Met Phe Thr
            580                 585                 590

Cys Leu Phe Leu Phe Ser Ala Val Leu Arg Ala Leu Phe Arg Lys Ser
            595                 600                 605

Asp Pro Lys Arg Phe Gln Asn Ile Phe Thr Thr Ile Phe Thr Leu Phe
            610                 615                 620

Thr Leu Leu Thr Leu Asp Asp Trp Ser Leu Ile Tyr Met Asp Ser Arg
625                 630                 635                 640

Ala Gln Gly Ala Trp Tyr Ile Ile Pro Ile Leu Ile Ile Tyr Ile Ile
            645                 650                 655

Ile Gln Tyr Phe Ile Phe Leu Asn Leu Val Ile Thr Val Leu Val Asp
            660                 665                 670

Ser Phe Gln Thr Ala Leu Phe Lys Gly Leu Glu Lys Ala Lys Gln Glu
            675                 680                 685

Arg Ala Ala Arg Ile Gln Glu Lys Leu Leu Glu Asp Ser Leu Thr Glu
            690                 695                 700

Leu Arg Ala Ala Glu Pro Lys Glu Val Ala Ser Glu Gly Thr Met Leu
705                 710                 715                 720

Lys Arg Leu Ile Glu Lys Lys Phe Gly Thr Met Thr Glu Lys Gln Gln
            725                 730                 735

Glu Leu Leu Phe His Tyr Leu Gln Leu Val Ala Ser Val Glu Gln Glu
            740                 745                 750
```

```
Gln Gln Lys Phe Arg Ser Gln Ala Ala Val Ile Asp Glu Ile Val Asp
        755                 760                 765

Thr Thr Phe Glu Ala Gly Glu Glu Asp Phe Arg Asn
        770                 775                 780

<210> SEQ ID NO 3
<211> LENGTH: 2061
<212> TYPE: DNA
<213> ORGANISM: Mus musculus
<220> FEATURE:
<223> OTHER INFORMATION: Murine Catsper 1

<400> SEQUENCE: 3
atggatcaat cttcaaggag ggacgagtct taccatgaga cacaccccgg tagcttagac      60
ccaagccatc aatcccaccc ccaccccac  ccccacccca ccctgcatag gccaaaccaa     120
ggtggcgtct attacgattc tcctcagcat gggatgttcc aacaaccata ccaacagcat     180
ggtgggttcc atcaacaaaa tgaattgcag catttgcgtg agttctcaga ctcccatgac     240
aatgctttct cccatcattc ctatcagcag acagggctg  gtgtctctac cttacctaat    300
aacatctctc acgcttatgg tggatcgcac ccccttgctg agtcccagca ctctggtgga    360
ccccagagtg gacctcgtat tgacccgaat catcatcccc accaagatga ccccatagaa    420
cccagtgaac ctttgtccca ccctcctct  actggcagcc accaagggac aacccatcaa     480
caataccatg agaggtctca ccatcttaac ccccagcaga acagagatca tgcagacacc    540
atttcctatc gctccagtac gcggttctat cgctcccatg cgccgttcag tcgccaggaa    600
agacctcatc tccacgctga tcaccatcat gagggccatc atgcccattc tcaccatggt    660
gaacatcccc accacaagga gcaacggcac tatcacggag atcatatgca tcaccatatc    720
catcatcgct ccccaagtgc ctcccaactc tcacacaagt ctcacagcac acttgccacc    780
tctccatctc atgtgggatc gaaaagcaca gccagtgggg ctcggtacac ctttggagct    840
cgctctcaaa ttttcggcaa agctcagtcc agggagagct tgagagaatc agcctctttg    900
agtgaagggg aggatcacgt tcagaaacgc aaaaaggccc agagggccca caagaaggca    960
cacaccggga atatcttcca attgctatgg aaaaaataa  gccatctcct tttgggtctt    1020
cagcaaatga tattgtcact gacccagtcc ctgggctttg agaccttttat cttcatcgtg   1080 gtctgcctca acacagtcat ccttgtggcc cagactttca ctgagctaga gatccgaggt   1140
gaatggtact tcatggtctt ggactccatc ttcctctcca tctatgtact agaagcagtc   1200
ctcaagctaa ttgccctggg cctggagtat tttatgacc  catggaacaa cctggacttc   1260
ttcatcatgg tcatggcagt gctggacttt gtgctccttc agataaactc gctctcatat   1320
tcattctaca ccacagcct  gttccggatt ctcaaagtct tcaaaagtat gcgggccctg    1380
agggccatcc gggttcttcg gaggctcagc atcctgacca gctccacga  agtggccggg    1440 actctgagtg gatctttacc atccatcacg gccatcctca ccctcatgtt tacctgcctc   1500
ttcctcttct ctgtggttct ccgagcactg tttcaggact cagacccaa  gcgcttccag    1560 aacatcttta ccacactctt cacccctgttc accatgctca ccctggacga ctggtccctc   1620
atctacatag acaacagggc ccaaggcgcc tggtacatca taccgatcct catgatttac   1680
attgtcatcc agtacttcat cttcctcaac ctggtgattg ctgtcctggt agataacttc   1740
cagatggcgt tgctcaaagg cctagagaaa gtgaagctgg agcaagctgc ccgggtccat   1800
gagaagttgt tggacgactc tctgacagat ctcaacaaag cagacgccaa tgcacaaatg   1860
accgaggagg ccttgaagat gcagcttatt gagggaatgt ttggcaacat gacagtgaag   1920
```

```
cagcgggtgc tccacttcca gttcctgcag ttggtggcag cggtagaaca gcatcaacag    1980
aagtttcgtt cccaagcgta cgtcatcgat gagcttgtgg acatggcatt tgaggctgga    2040
gacgacgact acgggaagtg a                                              2061
```

<210> SEQ ID NO 4
<211> LENGTH: 686
<212> TYPE: PRT
<213> ORGANISM: Mus musculus
<220> FEATURE:
<223> OTHER INFORMATION: Murine Catsper 1

<400> SEQUENCE: 4

```
Met Asp Gln Ser Ser Arg Arg Asp Glu Ser Tyr His Glu Thr His Pro
1               5                   10                  15

Gly Ser Leu Asp Pro Ser His Gln Ser His Pro His Pro His Pro His
            20                  25                  30

Pro Thr Leu His Arg Pro Asn Gln Gly Gly Val Tyr Tyr Asp Ser Pro
        35                  40                  45

Gln His Gly Met Phe Gln Gln Pro Tyr Gln Gln His Gly Gly Phe His
    50                  55                  60

Gln Gln Asn Glu Leu Gln His Leu Arg Glu Phe Ser Asp Ser His Asp
65                  70                  75                  80

Asn Ala Phe Ser His Ser Tyr Gln Gln Asp Arg Ala Gly Val Ser
                85                  90                  95

Thr Leu Pro Asn Asn Ile Ser His Ala Tyr Gly Gly Ser His Pro Leu
            100                 105                 110

Ala Glu Ser Gln His Ser Gly Gly Pro Gln Ser Gly Pro Arg Ile Asp
        115                 120                 125

Pro Asn His His Pro His Gln Asp Asp Pro His Arg Pro Ser Glu Pro
    130                 135                 140

Leu Ser His Pro Ser Ser Thr Gly Ser His Gln Gly Thr Thr His Gln
145                 150                 155                 160

Gln Tyr His Glu Arg Ser His His Leu Asn Pro Gln Gln Asn Arg Asp
                165                 170                 175

His Ala Asp Thr Ile Ser Tyr Arg Ser Ser Thr Arg Phe Tyr Arg Ser
            180                 185                 190

His Ala Pro Phe Ser Arg Gln Glu Arg Pro His Leu His Ala Asp His
        195                 200                 205

His His Glu Gly His His Ala His Ser His His Gly Glu His Pro His
    210                 215                 220

His Lys Glu Gln Arg His Tyr His Gly Asp His Met His His His Ile
225                 230                 235                 240

His His Arg Ser Pro Ser Ala Ser Gln Leu Ser His Lys Ser His Ser
                245                 250                 255

Thr Leu Ala Thr Ser Pro Ser His Val Gly Ser Lys Thr Ala Ser
            260                 265                 270

Gly Ala Arg Tyr Thr Phe Gly Ala Arg Ser Gln Ile Phe Gly Lys Ala
        275                 280                 285

Gln Ser Arg Glu Ser Leu Arg Glu Ser Ala Ser Leu Ser Glu Gly Glu
    290                 295                 300

Asp His Val Gln Lys Arg Lys Lys Ala Gln Arg Ala His Lys Lys Ala
305                 310                 315                 320

His Thr Gly Asn Ile Phe Gln Leu Leu Trp Glu Lys Ile Ser His Leu
                325                 330                 335
```

-continued

Leu Leu Gly Leu Gln Gln Met Ile Leu Ser Leu Thr Gln Ser Leu Gly
                340                 345                 350

Phe Glu Thr Phe Ile Phe Ile Val Val Cys Leu Asn Thr Val Ile Leu
            355                 360                 365

Val Ala Gln Thr Phe Thr Glu Leu Glu Ile Arg Gly Glu Trp Tyr Phe
370                 375                 380

Met Val Leu Asp Ser Ile Phe Leu Ser Ile Tyr Val Leu Glu Ala Val
385                 390                 395                 400

Leu Lys Leu Ile Ala Leu Gly Leu Glu Tyr Phe Tyr Asp Pro Trp Asn
                405                 410                 415

Asn Leu Asp Phe Phe Ile Met Val Met Ala Val Leu Asp Phe Val Leu
            420                 425                 430

Leu Gln Ile Asn Ser Leu Ser Tyr Ser Phe Tyr Asn His Ser Leu Phe
        435                 440                 445

Arg Ile Leu Lys Val Phe Lys Ser Met Arg Ala Leu Arg Ala Ile Arg
    450                 455                 460

Val Leu Arg Arg Leu Ser Ile Leu Thr Ser Leu His Glu Val Ala Gly
465                 470                 475                 480

Thr Leu Ser Gly Ser Leu Pro Ser Ile Thr Ala Ile Leu Thr Leu Met
                485                 490                 495

Phe Thr Cys Leu Phe Leu Phe Ser Val Val Leu Arg Ala Leu Phe Gln
            500                 505                 510

Asp Ser Asp Pro Lys Arg Phe Gln Asn Ile Phe Thr Thr Leu Phe Thr
        515                 520                 525

Leu Phe Thr Met Leu Thr Leu Asp Asp Trp Ser Leu Ile Tyr Ile Asp
    530                 535                 540

Asn Arg Ala Gln Gly Ala Trp Tyr Ile Ile Pro Ile Leu Met Ile Tyr
545                 550                 555                 560

Ile Val Ile Gln Tyr Phe Ile Phe Leu Asn Leu Val Ile Ala Val Leu
                565                 570                 575

Val Asp Asn Phe Gln Met Ala Leu Leu Lys Gly Leu Glu Lys Val Lys
            580                 585                 590

Leu Glu Gln Ala Ala Arg Val His Glu Lys Leu Leu Asp Asp Ser Leu
        595                 600                 605

Thr Asp Leu Asn Lys Ala Asp Ala Asn Ala Gln Met Thr Glu Glu Ala
    610                 615                 620

Leu Lys Met Gln Leu Ile Glu Gly Met Phe Gly Asn Met Thr Val Lys
625                 630                 635                 640

Gln Arg Val Leu His Phe Gln Phe Leu Gln Leu Val Ala Ala Val Glu
                645                 650                 655

Gln His Gln Gln Lys Phe Arg Ser Gln Ala Tyr Val Ile Asp Glu Leu
            660                 665                 670

Val Asp Met Ala Phe Glu Ala Gly Asp Asp Tyr Gly Lys
        675                 680                 685

<210> SEQ ID NO 5
<211> LENGTH: 926
<212> TYPE: DNA
<213> ORGANISM: Mus musculus
<220> FEATURE:
<223> OTHER INFORMATION: Mouse Catsper 1

<400> SEQUENCE: 5
gctagctccc tcttagtcct gtcctcagcg tgagggagcc catttacata gcaatgttga    60
gctcaacttg agataaccct gacattgtgg gaaatgccca agaaccactc ttcatggtcc    120

```
tgcggcagct tgccaattcc atggcctcag gctcaggcct gttcgtgagc ctggcggttt    180
cttcaggctt gaactacagt tgctggtttg tgtctgatgt ctgcttgatg aaaggactgg    240
tctgcagctg ctggttcatg tgtgtagtct gtatgcctag aggactggtc tgcagctgct    300
gagtcatatt tggtgtttgc tacaggactg aactgctgac aaagatcgaa ctcgtcccca    360
aagaactatt gctgaacagg tccacttccc ccagaccctg ataactttcc tctaacactg    420
cctctgctgg gtggtgagct agaggagagg ttaaacccct attaaaagta ggttgcaaaa    480
aatgtatgcc tacagtgtag ccctggttga cttggaactc attgtgtaga ccagacttga    540
gctcacagag atctacctgc ctctgcctcc ctagtgctgg gttcggggg ctttactatc     600 acacccagcc cagttttctg attttacaat aaagaggtga gtgagctatg ctaattcctt    660
ttcttcatct tttatttgtt tgggttttgt tttgtttaga cacaatagtt ctcaattctg    720
aatgataagc tcaaagaaag tcctcatttg taaagcgaga cctaagcaca ctgatgacat    780
catagaaagg aagattccga gagaagagtc agagctccct ggaagccggg gctgtggttg    840
gactgagctt ggcttgaggg gatcccgaga agggactttg ggttatacac ctgagctgtc    900
tttgttccag gggctccaag acagtc                                         926

<210> SEQ ID NO 6
<211> LENGTH: 498
<212> TYPE: DNA
<213> ORGANISM: Mus musculus
<220> FEATURE:
<223> OTHER INFORMATION: Mouse Catsper 1
<220> FEATURE:
<221> NAME/KEY: modified_base
<222> LOCATION: (445)..(445)
<223> OTHER INFORMATION: a, c, t or g
<220> FEATURE:
<221> NAME/KEY: modified_base
<222> LOCATION: (480)..(480)
<223> OTHER INFORMATION: a, c, t or g

<400> SEQUENCE: 6
ccctgaagaa tactaacctg agtttctggc aagctaccta cctcggtggg ttgggacatg     60
gccctaatgc tgctggtatt atccagaacc atgttggact gaggtcccaa tagagttttt    120 aaaaccccctg gagggctctg tgtccttact ggctagcctg aagcaaaggt caagaggcaa   180
tcgaatagtg tgccgtagac atatgttgaa agttgcttgt ggaagaggct cttcttggat    240
ctcctctgac ctcaccaggt tctagcctct gagttcagtc caacatgaca ttagcagaga    300
tcagaagagc ggtatagaaa gaggagcctg gggagaggat ggaagaccca ctgtgaagtc    360
ctttgatggg gagaacctgt ctgtcctggg gttgggagaa aaagaacag actgaaacag     420 tccagaactt tcagggttgc attanaggcc aggcatgggg ctcagcaccc aggaactcan    480
gcttaccagg aaccccaa                                                  498

<210> SEQ ID NO 7
<211> LENGTH: 27
<212> TYPE: PRT
<213> ORGANISM: Mus musculus

<400> SEQUENCE: 7

Arg Phe Gln Asn Ile Phe Thr Thr Leu Phe Thr Leu Phe Thr Met Leu
1               5                   10                  15

Thr Leu Asp Asp Trp Ser Leu Ile Tyr Ile Asp
            20                  25

<210> SEQ ID NO 8
```

```
<211> LENGTH: 27
<212> TYPE: PRT
<213> ORGANISM: Oryctolagus cuniculus

<400> SEQUENCE: 8

Asn Phe Asp Asn Phe Ala Phe Ala Met Leu Thr Val Phe Gln Cys Ile
1               5                   10                  15

Thr Met Glu Gly Trp Thr Asp Val Leu Tyr Asn
            20                  25

<210> SEQ ID NO 9
<211> LENGTH: 27
<212> TYPE: PRT
<213> ORGANISM: Homo sapiens

<400> SEQUENCE: 9

Asn Phe Asp Asn Ile Leu Phe Ala Ile Leu Thr Val Phe Gln Cys Ile
1               5                   10                  15

Thr Met Glu Gly Trp Thr Asp Ile Leu Tyr Asn
            20                  25

<210> SEQ ID NO 10
<211> LENGTH: 27
<212> TYPE: PRT
<213> ORGANISM: Rattus norvegicus

<400> SEQUENCE: 10

Asn Phe Asp Asn Ile Gly Tyr Ala Trp Ile Ala Ile Phe Gln Val Ile
1               5                   10                  15

Thr Leu Glu Gly Trp Val Asp Ile Met Tyr Phe
            20                  25

<210> SEQ ID NO 11
<211> LENGTH: 27
<212> TYPE: PRT
<213> ORGANISM: Oryctolagus cuniculus

<400> SEQUENCE: 11

Thr Phe Asp Asn Phe Pro Gln Ser Leu Leu Thr Val Phe Gln Ile Leu
1               5                   10                  15

Thr Gly Glu Asp Trp Asn Ser Val Met Tyr Asp
            20                  25

<210> SEQ ID NO 12
<211> LENGTH: 27
<212> TYPE: PRT
<213> ORGANISM: Homo sapiens

<400> SEQUENCE: 12

Asn Phe Asp Thr Phe Pro Ala Ala Ile Leu Thr Val Phe Gln Ile Leu
1               5                   10                  15

Thr Gly Glu Asp Trp Asn Ala Val Met Tyr Asn
            20                  25

<210> SEQ ID NO 13
<211> LENGTH: 27
<212> TYPE: PRT
<213> ORGANISM: Rattus norvegicus

<400> SEQUENCE: 13

Asn Phe Asp Ser Leu Leu Trp Ala Ile Val Thr Val Phe Gln Ile Leu
1               5                   10                  15

Thr Gln Glu Asp Trp Asn Lys Val Leu Tyr Asn
```

```
                  20                  25

<210> SEQ ID NO 14
<211> LENGTH: 27
<212> TYPE: PRT
<213> ORGANISM: Oryctolagus cuniculus

<400> SEQUENCE: 14

Asp Phe Asp Asn Val Leu Ala Ala Met Met Ala Leu Phe Thr Val Ser
1               5                   10                  15

Thr Phe Glu Gly Trp Pro Glu Leu Leu Tyr Arg
                  20                  25

<210> SEQ ID NO 15
<211> LENGTH: 27
<212> TYPE: PRT
<213> ORGANISM: Homo sapiens

<400> SEQUENCE: 15

His Tyr Asp Asn Val Leu Trp Ala Leu Leu Thr Leu Phe Thr Val Ser
1               5                   10                  15

Thr Gly Glu Gly Trp Pro Met Tyr Leu Lys His
                  20                  25

<210> SEQ ID NO 16
<211> LENGTH: 27
<212> TYPE: PRT
<213> ORGANISM: Rattus norvegicus

<400> SEQUENCE: 16

Asn Phe Asp Asn Leu Gly Gln Ala Leu Met Ser Leu Phe Val Leu Ala
1               5                   10                  15

Ser Lys Asp Gly Trp Val Asp Ile Met Tyr Asp
                  20                  25

<210> SEQ ID NO 17
<211> LENGTH: 27
<212> TYPE: PRT
<213> ORGANISM: Oryctolagus cuniculus

<400> SEQUENCE: 17

Asn Phe Gln Thr Phe Pro Gln Ala Val Leu Leu Leu Pro Arg Cys Ala
1               5                   10                  15

Thr Gly Glu Ala Trp Gln Asp Ile Met Leu Ala
                  20                  25

<210> SEQ ID NO 18
<211> LENGTH: 27
<212> TYPE: PRT
<213> ORGANISM: Homo sapiens

<400> SEQUENCE: 18

Asn Phe Arg Thr Phe Leu Gln Ala Leu Met Leu Leu Phe Arg Ser Ala
1               5                   10                  15

Thr Gly Glu Ala Trp His Glu Ile Met Leu Ser
                  20                  25

<210> SEQ ID NO 19
<211> LENGTH: 27
<212> TYPE: PRT
<213> ORGANISM: Rattus norvegicus

<400> SEQUENCE: 19
```

-continued

```
Thr Phe Arg Asn Phe Gly Met Ala Phe Leu Thr Leu Phe Arg Val Ser
1               5                   10                  15

Thr Gly Asp Asn Trp Asn Gly Ile Met Lys Asp
            20                  25

<210> SEQ ID NO 20
<211> LENGTH: 27
<212> TYPE: PRT
<213> ORGANISM: Homo sapiens

<400> SEQUENCE: 20

Arg Phe Gln Asn Ile Phe Thr Thr Leu Phe Thr Leu Phe Thr Met Leu
1               5                   10                  15

Thr Leu Asp Asp Trp Ser Leu Ile Tyr Ile Asp
            20                  25
```